(12) United States Patent
Frey, II

(10) Patent No.: US 9,707,274 B2
(45) Date of Patent: Jul. 18, 2017

(54) METHODS FOR PREVENTING AND TREATING POST-TRAUMATIC STRESS DISORDER (PTSD)

(71) Applicant: HealthPartners Research & Education, Bloomington, MN (US)

(72) Inventor: William H. Frey, II, White Bear Lake, MN (US)

(73) Assignee: HealthPartners Research & Education, Minneapolis, MN (US)

( * ) Notice: Subject to any disclaimer, the term of this patent is extended or adjusted under 35 U.S.C. 154(b) by 0 days.

(21) Appl. No.: 14/040,915

(22) Filed: Sep. 30, 2013

(65) Prior Publication Data

US 2014/0031280 A1  Jan. 30, 2014

Related U.S. Application Data

(63) Continuation-in-part of application No. 12/134,385, filed on Jun. 6, 2008.

(60) Provisional application No. 61/718,860, filed on Oct. 26, 2012, provisional application No. 60/942,696, filed on Jun. 8, 2007.

(51) Int. Cl.
*A61K 38/28* (2006.01)
*A61K 31/4164* (2006.01)
*A61K 45/06* (2006.01)
*A61K 33/24* (2006.01)
*A61K 31/137* (2006.01)
*A61K 9/00* (2006.01)

(52) U.S. Cl.
CPC ............ *A61K 38/28* (2013.01); *A61K 9/0043* (2013.01); *A61K 31/137* (2013.01); *A61K 31/4164* (2013.01); *A61K 33/24* (2013.01); *A61K 45/06* (2013.01)

(58) Field of Classification Search
CPC .... A61K 2300/00; A61K 38/28; A61K 38/30; A61K 9/0043
See application file for complete search history.

(56) References Cited

U.S. PATENT DOCUMENTS

| | | | |
|---|---|---|---|
| 2,989,437 A | 6/1961 | Wruble et al. | |
| 5,135,923 A | 8/1992 | Siren | |
| 5,624,898 A | 4/1997 | Frey, II | |
| 5,849,290 A | 12/1998 | Brown et al. | |
| 5,874,573 A | 2/1999 | Winchell et al. | |
| 5,939,395 A | 8/1999 | Yu et al. | |
| 6,113,906 A | 9/2000 | Greenwald et al. | |
| 6,180,603 B1 | 1/2001 | Frey, II | |
| 6,313,093 B1 | 11/2001 | Frey, II | |
| 6,342,478 B1 | 1/2002 | Frey, II | |
| 6,407,061 B1 | 6/2002 | Frey, II | |
| 6,413,499 B1 | 7/2002 | Clay | |
| 6,544,542 B1 | 4/2003 | Sonoke et al. | |
| 6,576,660 B1 | 6/2003 | Liao et al. | |
| 6,991,785 B2 | 1/2006 | Frey, II | |
| 7,084,126 B1 | 8/2006 | Frey, II et al. | |
| 7,112,566 B1 | 9/2006 | Siegel et al. | |
| 2001/0043915 A1 | 11/2001 | Frey, II | |
| 2001/0047032 A1 | 11/2001 | Castillo et al. | |
| 2002/0028786 A1* | 3/2002 | Frey, II ................ | A61K 31/352 514/48 |
| 2002/0072498 A1 | 6/2002 | Frey, II | |
| 2002/0082215 A1 | 6/2002 | Frey, II | |
| 2002/0141971 A1 | 10/2002 | Frey, II | |
| 2003/0072793 A1 | 4/2003 | Frey, II et al. | |
| 2003/0133877 A1 | 7/2003 | Levin | |
| 2003/0165434 A1 | 9/2003 | Reinhard et al. | |
| 2003/0229025 A1 | 12/2003 | Xiao et al. | |
| 2004/0101521 A1 | 5/2004 | Andersen | |
| 2004/0229794 A1 | 11/2004 | Ryan et al. | |
| 2005/0031651 A1 | 2/2005 | Gervais et al. | |
| 2006/0039995 A1 | 2/2006 | Frey, II et al. | |
| 2007/0004743 A1 | 1/2007 | Xiao et al. | |
| 2007/0021331 A1 | 1/2007 | Fraser et al. | |
| 2007/0054843 A1 | 3/2007 | Yeomans et al. | |
| 2007/0092500 A1 | 4/2007 | Frey, II et al. | |

FOREIGN PATENT DOCUMENTS

| | | |
|---|---|---|
| WO | WO90/00057 | 1/1990 |
| WO | WO91/07947 | 6/1991 |
| WO | WO98/42275 | 10/1998 |
| WO | WO2007/025249 | 3/2007 |
| WO | WO2007/025286 | 3/2007 |

OTHER PUBLICATIONS

Benedict et al. 2004 "intranasal insulin improves memory in humans" Psychoneuroendocrinology 29:1326-1334.*
Fawcett et al 2002 "Inactivation of the human brain muscarinic acetylcholine receptor by oxidative damage catalyzed by a low molecular weight endogenous inhibitor from Alzheimer's brain is prevented by pyrophosphate analogs, bioflavinoids and other antioxidants" Brain research 950:10-20.*
Garg et al 2005 "Insulin glulisine: a new rapid-acting insulin analogue for the treatment of diabetes" Expert opin pharmacother (6(4):643-51 (abstract only).*
Gilbertson et al 2001 "Multivariate assessment of explicit memory function in combat veterans with posttraumatic stress disorder" J trauma Stress 14(2):413-32 (abstract only).*

(Continued)

*Primary Examiner* — Adam M Weidner
(74) *Attorney, Agent, or Firm* — Barnes & Thornburg LLP; Jeffrey R. Stone

(57) ABSTRACT

Methods for preventing and/or treating symptoms of Post-Traumatic Stress Disorder (PTSD) are provided. The preferred method comprises administration of an effective amount of insulin to the upper one-third of a mammal's, preferably a human, nasal cavity, thereby enabling the administered at least one effective amount of insulin to bypass the patient's blood-brain barrier and be directly delivered to the patient's CNS. Another embodiment comprises utilizing vasoconstrictors to enhance targeting of an effective amount of insulin to the CNS while reducing non-target exposure.

19 Claims, 5 Drawing Sheets

(56) References Cited

OTHER PUBLICATIONS

Jarvinen and Urtti 1992 "Duration and long-term efficacy of phenyephrine-induced reduction in the systemic adsorption of ophthalmic timolol in rabbits" J Ocul Pharmacol 8(2):91-8 (abstract only).*
Zieker et al 2007 "Differential gene expression in peripheral blood of patients suffering from post-traumatic stress disorder" Molecular Psychiatry 12:116-119.*
NYTimes 1992 "The doctors world; alzheimer's dilemma: whether to tell people they have the disease" New York Times by Lawrence Altman.*
ADAA 2015 "Test Anxiety" accessed from adaa.org on Sep. 4, 2015.*
FBI 2015 "Crime in the United States 2011" accessed from fbi.gov on Sep. 3, 2015.*
Standford 2015 "Passive avoidance task" accessed from sbfnl.stanford.edu on Sep. 4, 2015.*
Wikipedia 2015 "earthquake prediction" accessed from wikipedia.org on Sep. 3, 2015 (excerpt only).*
Stanford 2001 "Coronary artery bypass graft surgery" acessed from stanfordhealthcare.org.*
Dezhi et al., "HIF1 alpha upregulation and neuroprotection with deferoxamine in a rat neonatal stroke model" *Pediatric Research*, 55(4): 408A (Apr. 2004).
Ross et al., Intranasal administration of interferon beta bypasses the blood-brain to target the central nervous system and cervical lymph nodes: a non-invasive treatment strategy for multiple sclerosis, *Journal of Neuroimmunology*, 151(1-2): 66-67 (Jun. 2004).
Trinchese et al., Ann Neurol, 55:801-814, 2004.
House et al., J. Aiz Dis., 6(3):291-301, 2004.
Morse et al., J. Mol Neurosci, 24:129-136, 2004.
Adachi et al (Brit J Rheumatol 36:255-259, 1997).
Järvinen K and Uritti A. Duration and long-term efficacy of phenylephrine-induced reduction in the systemic absorption of ophthalmic timolol in rabbits. J Ocul. Pharmacol. 1992; 8(2):91-98; abstract only.
Vachharajani NN et al. A pharmacokinetic interactioni study between butorphanol and sumatriptan nasal sprays in healthy subjects: importance of the timing of butorphanol administration. Cephalalgia, 2002; 22:282-287.
Kruck et al., Clin Pharmacol Ther, 48(4): 439-446, Oct. 1990.
Gordon et al., Amer J Med Sci, 297(5): 280-284, May 1989.
Wang and Semenza, Blood, 82(12): 3610-3615, Dec. 15, 1993.
P. Murali Doraiswamy and Anne E. Finefrock, Metals in our minds: therapeutic implications for neurodegenerative disorders, The Lancet Neurology vol. 3, Jul. 2004 (pp. 431-434).
R.G. Thorne, et al., Delivery of Insulin-Like Growth Factor-I to the Rate Brain and Spinal Cord Along Olfactory and Tridgeminal Pathways Following Intranasal Administration, Neuroscience 127 (2004) (pp. 481-496).
Maxwell and Salniknow, Cancer Biology and Therapy 3(1): 29-35. (Jan. 2004).
Brenneisen et al., The Journal of Biological Chemistry 273(9): 5279-5287. (Feb. 27, 1998).
Crapper McLachlan et al., Lancet 337(8753): 1304-1308. (Jun. 1, 1991).
Chaston and Richardson, American Journal of Hematology 73: 200-210 (2003).
King RG, Med J Aust, 142(6; 352, Mar. 18, 1985).
Youdin et al., Ann NY Acad Sci, 1012:306-325, Mar. 2004.
Lan and Jiang, J Neural Transmission, 104:469-481, 1997.
Charlton S.T.; David S.S.; Ilium L.: "Evaluation of effect of ephedrine on the transport of drugs from the nasal cavity to the systemic circulation and the central nervous system", Journal of Drug Targeting, col. 15, No. 5, May 31, 2007 (May 31, 2007), pp. 370-377, XP9157742, ISSN: 1061-186X, DOI: DOI:10, 1080/10611860701393370.
S. Talegaonkar, P.A. Mishra, Intranasal delivery: An approach to bypass the blood brain barrier, Indian J. Phermacol, Jun. 2004, vol. 36, Issue 3 140-147.
Gould et al., "Glycogen Synthase Kinase-3: A Target for Novel Bipolar Disorder Treatment," Jan. 31, 2004 (Jan. 31, 2004). The Journal of Clinical Psychiatry, vol. 65, Is. 1; p. 1021; especially abstract; p. 13, col. 2, para 3; p. 15, col. 1, para 4 to col. 2, para 1; p. 17, col. 1, para 2.
The Merck Index, Twelfth Edition, 1996, entries 3908 and 7135.
Venters Jr., Homer D. et al., "Heme from Alzheimer's brain inhibits muscarinic receptor binding via thiyl radical generation" Brain Research, 1997, 764, 93-100.
Kornberg, Arthur, et al.; "Inorganic Polyphosphate: A Molecule of Many Functions"; Annual Review Biochemistry, vol. 68: 89-125; Annual Reviews; US 1999.
Frey II, William H. et al.,; "Brain Research 714 (1996) 87-94: Endogenous Alzheimer's brain factor and oxidaized glutathione inhibit antagonist binding to the muscarinic receptor"; Elsevier Science B.V.; US 1996.
Frey II, William H. et al., "Brain Research 655 (1994) 153-160: Inhibitor of antagonist binding to the muscarinic receptor is elevated in Alzheimer's brain"; Elsevier Science B.V.; US 1994.
Otterbein, Leo E., et al.; "Invited Review: Heme Oxygenase: colors of defense against cellular stress"; The American Physiological Society; www.aiplung.org: US2000.
Rogers et al (Arch Intern Med 158:1021-1031, 1998).
van Beek et al (Biochem Biophys Res Comm 255:491-494, 1999).
Pahan et al (J Clin Invest 100:2671-2679, 1997).
Zhao et al (J Neurosci Res 52:7-16, 1998).
Fawcett et al (Brain Res 950:10-20, 2002).
Atack et al (J Neurochem 60:652-658, 1993).
Liu et al., Molecular and Cellular Biology, Sep. 1992, 3978-3990.
Frey et al., "Delivery of 125I-NGF to the Brain via the Olfactory Route", Drug Delivery, 4:87-92, 1997.
Ostovic et al (Pharm Res 10:470-472, 1993).
Rooijen (Calcif Tissue Int 52:407-410, 1993).
Body et al (Annals of Oncology, 5:359-363, 1994; Abstract Only).
Backstrom et al (J Neurosci 16:7910-7919, 1996).

* cited by examiner

FIGURE 1: BLOOD CONCENTRATION OF HC FOLLOWING DIFFERENT PRETREATMENT TIME INTERVALS
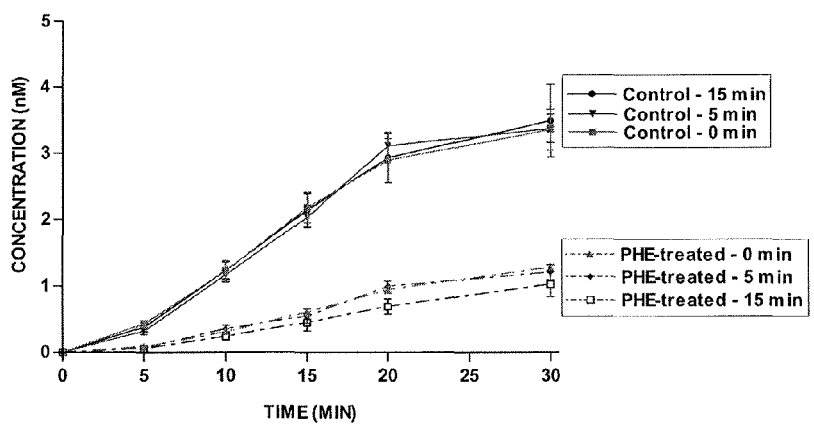
FIGURE 2: BLOOD CONCENTRATION OF HC AFTER MERGING PRETREATMENT TIME INTERVAL DATA
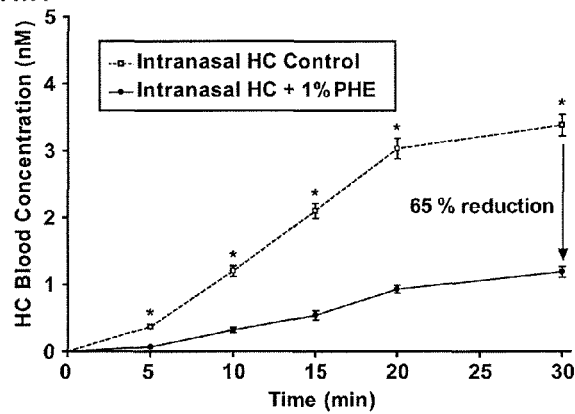

FIGURE 3: CNS TISSUE-TO-BLOOD CONCENTRATION RATIOS OF HC FOLLOWING INTRANASAL ADMINISTRATION IN THE PRESENCE AND ABSENCE OF 1% PHE

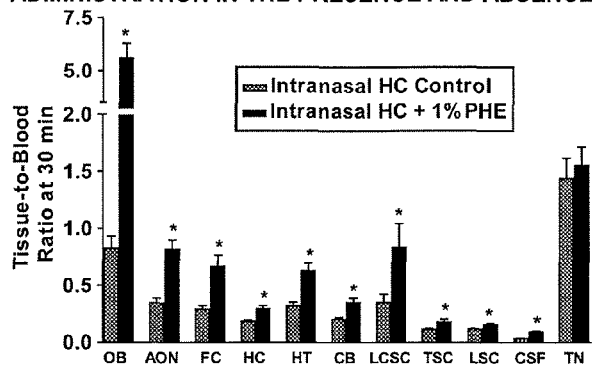

OB = olfactory bulbs, AON = anterior olfactory nucleus, FC = frontal cortex, HC = hippocampus, HT = hypothalamus, CB = cerebellum, LCSC = lower cervical spinal cord, TSC = thoracic spinal cord, CSF = cerebrospinal fluid, TN = trigeminal nerve FIGURE 4: BLOOD CONCENTRATION OF TP FOLLOWING INTRANASAL ADMINISTRATION IN THE PRESENCE AND ABSENCE OF 1% PHE
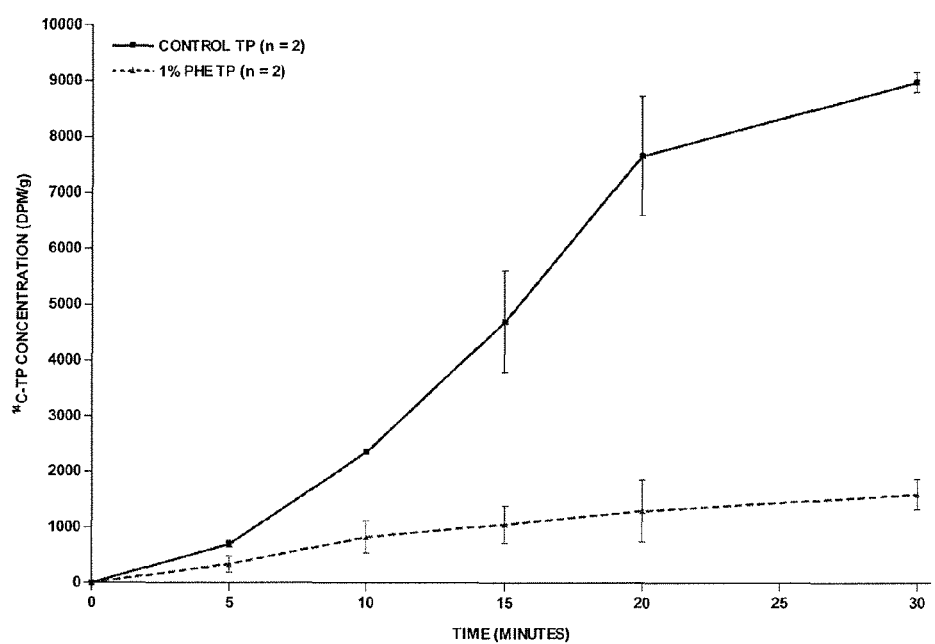

FIGURE 5: CONCENTRATIONS OF TP IN PERIPHERAL TISSUES IN THE PRESENCE AND ABSENCE OF 1% PHE
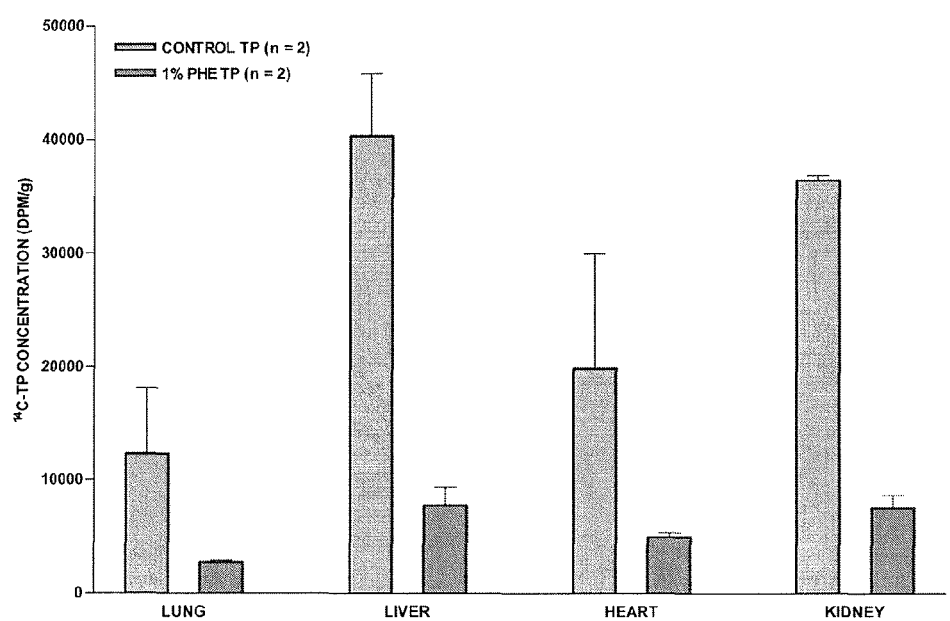

FIGURE 6: BLOOD CONCENTRATION OF KTP FOLLOWING INTRAVENOUS ADMINISTRATION AND INTRANASAL ADMINISTRATION IN THE PRESENCE AND ABSENCE OF PHE

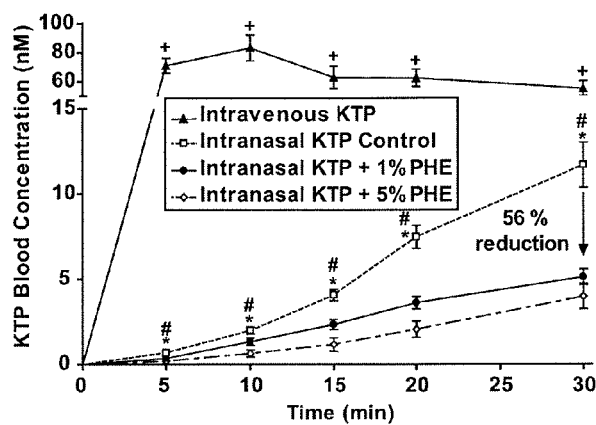

FIGURE 7: CNS TISSUE-TO-BLOOD CONCENTRATION RATIOS OF KTP FOLLOWING INTRAVENOUS ADMINISTRATION AND INTRANASAL ADMINISTRATION IN THE PRESENCE AND ABSENCE OF PHE

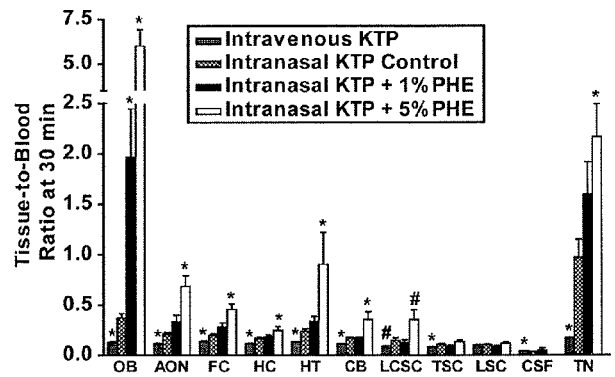

OB = olfactory bulbs, AON = anterior olfactory nucleus, FC = frontal cortex, HC = hippocampus, HT = hypothalamus, CB = cerebellum, LCSC = lower cervical spinal cord, TSC = thoracic spinal cord, CSF = cerebrospinal fluid, TN = trigeminal nerve

METHODS FOR PREVENTING AND TREATING POST-TRAUMATIC STRESS DISORDER (PTSD)

CROSS-REFERENCE TO RELATED APPLICATIONS

The present application claims priority to provisional application No. 61/718,860, filed on Oct. 26, 2012 entitled METHODS OF TREATING AND PREVENTING POST-TRAUMATIC STRESS DISORDER BY INTRANASAL INSULIN, the entire contents of which are incorporated herein by reference and is a continuation-in-part of application Ser. No. 12/134,385, filed on Jun. 6, 2008, entitled PHARMACEUTICAL COMPOSITIONS AND METHODS FOR ENHANCING TARGETING OF THERAPEUTIC COMPOUNDS TO THE CENTRAL NERVOUS SYSTEM and which claims priority to provisional application 60/942,696, filed Jun. 8, 2007, entitled PHARMACEUTICAL COMPOSITIONS AND METHODS FOR ENHANCING TARGETING OF THERAPEUTIC COMPOUNDS TO THE CENTRAL NERVOUS SYSTEM.

BACKGROUND OF THE INVENTION

Field of the Invention

The present disclosure generally relates to methods of treating and preventing posttraumatic stress disorder (PTSD) in humans. More particularly, the present disclosure is directed to a method of treating and preventing PTSD, and the like by administration of intranasal insulin to the upper one-third of a patient's nasal cavity.

Description of the Related Art

Posttraumatic stress disorder (PTSD) is a severe anxiety central nervous system disorder that may develop in response to exposure to an event resulting in psychological trauma. PTSD may be less frequent and more enduring than the more commonly seen posttraumatic stress. PTSD is believed to be triggered by a subject witnessing or experiencing any of a wide range of events that produce intense negative feelings of fear, helplessness, or horror. This experienced fear may trigger many split-second changes in the body to prepare to defend against or avoid the danger. The "fight-or-flight" response is a healthy reaction meant to protect a person from harm. But it is believed that with PTSD, this reaction is altered. People suffering from PTSD may feel stressed or frightened even when they are not in danger. PTSD symptoms may include reliving the traumatic event in the form of flashbacks, or nightmares, for example. Further, symptoms of PTSD may include avoidance of places or things that are reminders of the experience; feeling emotionally numb; feeling anxious; and/or losing interest in formerly enjoyable activities. People suffering from PTSD may also experience hyperarousal symptoms such as being easily startled; feeling tense; and having difficulty sleeping for example.

If these symptoms are experienced for no more than a few weeks, the disorder may be referred to as acute stress disorder, or ASD. If the symptoms last more than a few weeks and become an ongoing problem, they might be diagnosed as PTSD. Some people with PTSD have few or no symptoms for weeks or even months following the event.

The main treatments for people with PTSD include psychotherapy, medications, or both. Sertraline (Zoloft®) and paroxetine (Paxil®), both of which are antidepressants, have been approved by the FDA for treating people with PTSD and are administered systemically, typically orally. The most common side effects of antidepressants like sertraline and paroxetine, also administered systemically, include: headache, nausea, agitation, sexual problems, and/or sleeplessness or drowsiness. Other types of systemically-administered medications may also be prescribed for people suffering from PTSD, such as benzodiazepines, antipsychotics, or other antidepressants. There is little information on how well these medications work for people with PTSD.

Further, the known medications are not necessarily targeting the physiological areas of the brain directly affected by PTSD and the known medications have side effects. The primary reason for this is that known medications are administered systemically, generally orally. Since the biological conditions leading to PTSD occur within the CNS and require treatment within the CNS, only a small percentage of each, e.g., orally, systemically administered dose of the medications discussed above will actually reach the CNS. This is due to several factors, some of which include: the medication in the patient's bloodstream goes through metabolic changes, some of the medication will be removed by the liver and other organs and/or be highly susceptible to protein binding, and the medication must also then cross the blood-brain barrier (BBB), which excludes most medium to large molecules. Accordingly, an excessively large dose of the medication must be administered systemically in order to achieve the therapeutic dose or concentration within the patient's CNS. This excessive dosing is undesirable as the patient's system, including organs and tissues are exposed to the medication and may be adversely affected, even dangerously affected.

Accordingly, a need exists for a therapeutic agent(s) or compound(s) that may be used to treat and/or prevent PTSD and other like disorders, which can be administered with a therapeutic dose, i.e., an effective amount of the therapeutic agent(s), that is delivered directly and targeted to the CNS for the treatment of PTSD and/or to help protect the brain from damage due to traumatic psychological stress which helps prevent PTSD while minimizing systemic exposure to the therapeutic agent or compound. Further, a need exists for such a therapeutic agent or compound that minimizes the adverse side effects generally associated with administration of drugs used to treat PTSD. Still further, a need exists for a delivery system for such a composition that provides for enhanced uptake of the composition to maximize the therapeutic effect obtained per administration.

Further, it is known that intranasal administration of therapeutic compounds or agents may, in some cases, increase the effectiveness of certain therapeutic compounds or agents in bypassing the blood brain barrier (BBB) and delivering the compound or agent directly to the CNS. Thus, intranasal administration of therapeutic compounds may allow increased prevention and/or treatment of certain diseases or conditions.

It is also known that greater than 98% of small molecule and nearly 100% of large molecule CNS drugs developed by the pharmaceutical industry do not cross the BBB. Intracerebroventricular or intraparenchymal drug administration can directly deliver therapeutics to the brain; however, these methods are invasive, inconvenient, and impractical for the numbers of individuals requiring therapeutic interventions for treating CNS disorders. Intranasal drug administration to the upper one-third of the patient's nasal cavity is a non-invasive and convenient means to rapidly target therapeutics of varying physical and chemical properties to the CNS. The olfactory and trigeminal neural pathways connecting the nasal passages to the CNS are clearly involved in the delivery of therapeutic compounds applied via intranasal administration to the upper third of the nasal cavity. In addition to these neural pathways, perivascular pathways, and pathways involving the cerebrospinal fluid or nasal lymphatics may play a central role in the distribution of therapeutics from the nasal cavity to the CNS.

The general intranasal method of drug delivery, i.e., administration to the lower two-thirds of the patient's nasal cavity, holds great promise as an alternative to more invasive routes, however, a number of factors limit the efficiency of general intranasal delivery to the CNS. Absorption of intranasally applied drugs into the capillary network in the nasal mucosa can decrease the amount of drug available for direct transport into the CNS. Additional factors within the nasal cavity, including the presence of nasal mucociliary clearance mechanisms, metabolizing enzymes, efflux transporters and nasal congestion can also reduce the efficiency of delivery into the CNS. In particular, therapeutic compounds may be absorbed into the blood and/or delivered to peripheral (non-target) tissues, thus reducing delivery of the compound to the target. As a result, the efficacy of administering therapeutic compounds to the lower two-thirds of the nasal cavity with the goal of delivering therapeutics to the CNS is greatly diminished. Further, the efficacy of administering therapeutic compounds to the upper one-third of the nasal cavity as a means to target therapeutics to the CNS could also be improved.

The method of administration of insulin to the upper one-third of the nasal cavity for treatment of neurodegenerative disorders, specifically Alzheimer's disease, provides the basis for the present invention. Insulin has been shown to improve memory in healthy adults, with no change in blood levels of insulin or glucose. See, e.g., Benedict C., et al (2004), Intranasal insulin improves memory in humans, Psychoneuroendocrinology, 29:1326-1334; Craft (2012), Alzheimer disease: Insulin resistance and AD—Extending the translational path. Nat Rev Neurol. 8:360-362; Reger et al., (2006), Effects of intranasal insulin on cognition in memory in memory-impaired older adults: Modulation by APOE genotype. Neurobiol Aging. 27:451-458; Reger, et al., (2008), Intranasal insulin improves cognition and modulates beta-amyloid in early AD, Neurology. 70-440-448.

Insulin is an effective treatment of Alzheimer's disease because glucose uptake and use are significantly decreased in patients with Alzheimer's disease. See de Leon, et al., (1997), Cortisol reduces hippocampal glucose metabolism in normal elderly, but not in Alzheimer's disease. J Clin Endocrinol Metab., 82:3251-3269. Glucose is the only source of energy used by brain cells under normal conditions, and the brain cells of patients with Alzheimer's disease are starved for energy. Alzheimer's disease has been reported to involve a deficiency of insulin and insulin signaling in the brain.

However, insulin is far more than simply a treatment agent for Alzheimer's symptoms. When insulin reaches the brain, it stimulates the formation of insulin-degrading enzyme, which is capable of degrading beta amyloid, one of the principal abnormal proteins known to accumulate in the brains of patients with Alzheimer's disease. Further, the activity of glycogen-synthase kinase-3-beta, the enzyme that phosphorylates tau to create Alzheimer's disease neurofibrillary tangles, has been reported to be downregulated in response to insulin. Finally, insulin receptor signaling increase synaptic density, and loss of synapses is key to the neuropathology of Alzheimer's disease.

Alzheimer's disease and PTSD have several relevant things in common. First, both disorders are characterized by elevations in blood levels of cortisol which can increase beta amyloid and tau pathology in rodent models of Alzheimer's disease. In patients with Alzheimer's disease, increased plasma cortisol levels are associated with more rapid disease progression. Second, the hippocampus, an area key to memory and emotional response, is damaged by elevated cortisol that inhibits the uptake of glucose needed by brain cells for energy. Hippocampal degeneration is common in Alzheimer's disease and has also been reported in patients with PTSD. Third, FDG-PET imaging reveals decreased uptake and utilization of glucose in both patients with AD (Li et al., 2008) and those with PTSD, although results with PTSD appear to be more variable. Finally, deficits in verbal declarative memory have been reported in patients with PTSD and short-term memory deficits are characteristic of patients with Alzheimer's disease.

Stress has been found to reduce the uptake and use of glucose by brain cells. See Sapolsky (1986), Glucocorticoid toxicity in the hippocampus: Reversal by supplementation with brain fuels. J Neurosci. 6:2240-2244. Multiple mechanisms are likely involved in this action, one of which is the inhibition of glucose use in the hippocampus by glucocorticoids. Cortisol has been reported to reduce hippocampal glucose use in healthy elderly adults on the basis of examination of the brain glucose use response to hydrocortisone. It is likely that glucocorticoids also reduce the capacity of the hippocampus to survive neurological insults because glucocorticoids inhibit glucose transport 15% to 30% in both primary and secondary hippocampal astrocytic cultures; this could impair the ability of astrocytes to aid neurons by removing damaging glutamate from the synapse during times of neurological crisis. Virgin, et al, (1991), Glucocorticoids inhibit glucose transport and glutamate uptake in hippocampal astrocytes: Implications for glucocorticoid neurotoxicity, J Neurochem. 57:1422-1428.

Mean cerebrospinal (CSF) cortisol concentrations are significantly higher in combat veterans with PTSD than in healthy comparison subjects. Baker et al, (2005), Higher levels of basal serial CSF cortisol in combat veterans with posttraumatic stress disorder, Am J Psychiatry. 5:992-994. Thus, cortisol levels are higher in individuals diagnosed with PTSD.

Further, in a study assessing the cortisol response to a cognitive challenge, patients with PTSD had 61% higher group mean cortisol levels in the time leading up to the cognitive challenge. Thus, cortisol levels are higher for individuals anticipating a stressing challenge. In this same study, the PTSD patients had cortisol levels 46% higher than the controls. Bremner et al, (2003), Cortisol response to a cognitive stress challenge in posttraumatic stress disorder (PTSD) related to childhood abuse. Psychoneuroendocrinology 28:733-750. And, recently, glucocorticoids have been shown to induce PTSD-like memory impairments in mice. Kaouane N (2012) Glucocorticoids can induce PTSD-like memory impairments in mice. Science, 335:1510-1513.

It would be desirable to provide a method of preventing and/or treating PTSD by directly delivering an effective amount of PTSD to the target within the patient's CNS. It would also be desirable to reduce absorption of intranasally-administered therapeutic compounds or agents, in this case insulin, for prevention and treatment of PTSD, into the blood and delivery to non-target or peripheral tissues. It would be further desirable to increase deposition and delivery of the therapeutic compounds or agents to, inter alia, the CNS, e.g., within the olfactory epithelium, the olfactory bulbs as well as the lymphatic system, and it would be desirable to increase therapeutic compound targeting relative to the blood to the frontal cortex, anterior olfactory nucleus, hippocampus, hypothalamus, pons, midbrain, medulla, cerebellum and to the meninges. It would be further desirable to provide an intranasal delivery method and pharmaceutical composition(s) that are effective and efficient in facilitating delivery, and maximum efficiency of delivery, of therapeutic compounds, e.g., insulin, to the CNS.

The present invention addresses, inter alia, these issues.

BRIEF SUMMARY OF THE INVENTION

The present system is directed in one embodiment to a method of administration of a therapeutic composition for treatment and prevention of posttraumatic stress disorder (PTSD). The method includes administering one or more therapeutic agent(s) or composition(s) comprising insulin to the upper third of a patient's nasal cavity, thereby delivering the therapeutic composition directly to the patient's central nervous system for treatment and/or prevention of PTSD. In still another embodiment, the therapeutic composition comprises a non-zinc containing form of insulin.

In still another embodiment, the insulin formulation is preserved with pyrophosphate or one of its analogues and may be prepared as a unit dose. In still another embodiment, the non-zinc containing insulin is formulated as a unit does that does not contain a cresol or a phenol preservative.

In certain embodiments, vasoconstrictor compounds for enhancing targeting to the CNS of therapeutic compounds such as insulin by reducing system exposure of same may be provided. Such vasoconstrictors may be applied via intranasal administration, either general (lower two-thirds of the patient's nasal cavity) or administration to the upper one third of the patient's nasal cavity in order to reduce non-target, i.e., systemic, exposure.

In certain embodiments, at least one vasoconstrictor is provided intranasally prior to intranasal administration of at least one therapeutic compound, e.g., insulin. In other embodiments, the vasoconstrictor(s) and therapeutic compound(s), e.g., insulin, are combined in a pharmaceutical composition and delivered intranasally. The present invention substantially increases targeting of the therapeutic compound(s), e.g., insulin, to the CNS while substantially reducing unwanted and potentially harmful systemic exposure. A preferred administration of this form and embodiment of the invention applies the vasoconstrictor(s) and/or therapeutic compound(s) comprising insulin to the upper third of the nasal cavity, though application to the lower two-thirds of the nasal cavity is also within the scope of the invention.

An object of the present invention comprises administering an effective amount of insulin to the upper third of a patient's nasal cavity, thereby enabling the effective amount of insulin to bypass the patient's blood-brain barrier, thus directly delivering the effective amount of insulin to the patient's CNS, i.e., brain for the prevention and/or treatment of PTSD in the patient.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying Figures and Tables included herein.

FIG. 1 is a graph of the blood concentration of a therapeutic agent in a subject after pretreatment with a vasoconstrictor;

FIG. 2 is an alternate presentation of the blood concentration of the blood concentration of a therapeutic agent in a subject after pretreatment with a vasoconstrictor;

FIG. 3 is a graph of blood-to-tissue ratios of a therapeutic agent in the presence and absence of a vasoconstrictor;

FIG. 4 is a graph of the blood concentration of a therapeutic agent in the presence and absence of a vasoconstrictor;

FIG. 5 is a graph of the peripheral tissue concentration of a therapeutic agent in the presence and absence of a vasoconstrictor.

FIG. 6 is a graph of the blood concentration of a therapeutic agent in the presence and absence of a vasoconstrictor; and FIG. 7 is a graph of blood-to-tissue ratios of a therapeutic agent in the presence and absence of a vasoconstrictor.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

DEFINITIONS

As used herein, "central nervous system" (CNS) refers to the brain and spinal cord and associated tissues.

As used herein, "drug targeting" refers to increasing drug concentration in a tissue relative to the concentration of that drug in the blood.

As used herein, "efficiency" refers to targeting specificity of the drug, i.e., therapeutic compound to a particular physiological location, delivery with minimal residual loss to non-target physiological locations, or both.

As used herein, "meninges" refers to the dura, pia and arachnoid membranes surrounding the brain and spinal cord.

As used herein, "brainstem" refers to the pons, medulla and midbrain.

An "effective amount" of therapeutic compound or agent such as insulin or a vasoconstrictor is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and, perhaps, overcome the disease itself.

In the context of the present invention, the terms "treat" and "therapy" and "therapeutic" and the like refer to alleviate, slow the progression, prophylaxis, attenuation or cure PTSD other CNS-related disease and/or condition.

"Prevent", as used herein, refers to putting off, delaying, slowing, inhibiting, or otherwise stopping, reducing or ameliorating the onset of PTSD other CNS-related disease and/or condition. It is preferred that a large enough quantity of the agent be applied in non-toxic levels in order to provide an effective level of neuroprotection. The method of the present invention may be used with any animal, such as a mammal or a bird (avian), more preferably a mammal. Poultry are a preferred bird. Exemplary mammals include, but are not limited to rats, cats, dogs, horses, cows, sheep, pigs, and more preferably humans.

"Intranasal Delivery" as used herein, refers to the application, delivery and/or administration of at least one therapeutic agent or compound, at least one vasoconstrictor and/or a combination thereof, i.e., pharmaceutical composition, to the nasal cavity of the subject. Such intranasal delivery comprises application, delivery and/or administration of the compound(s), vasoconstrictor(s) and/or pharmaceutical composition to the entire nasal cavity, the upper one-third of the nasal cavity and/or the lower two-thirds of the nasal cavity. When upper one-third administration is preferred or required, it will be specified.

The present disclosure is generally directed to administering insulin intranasally to the upper one-third of a mammal's nasal cavity. An exemplary mammal is a human being. Certain individuals in certain professions or occupations experience highly stressful events more frequently than people in other professions. One of the objects of the present invention is to administer a treatment or preventative to people in these high-stress professions, wherein these people may suffer from, or may be likely to suffer from PTSD. Similarly, other people suffering from PTSD, such as victims of assault, rape, or other forms of abuse, or people that survived life-threatening accidents or events or natural disasters, for example, may also benefit from a treatment or preventative that may relieve or eliminate or prevent the symptoms associated with PTSD. The administration of intranasal insulin to the upper one-third of an individual's nasal cavity wherein that individual is suffering from, or likely to suffer from PTSD may help treat and/or prevent some or all of the symptoms associated with PTSD, in accordance with embodiments of the present disclosure.

In some embodiments, the therapeutic agent—insulin—may be combined with a vasoconstrictor to be administered intranasally to limit systemic exposure. The vasoconstrictor may be administered to the nasal cavity prior to administration of the therapeutic compound to the upper third of the nasal cavity or, alternatively, the vasoconstrictor and therapeutic compound may be administered concurrently. In any case, the effective amount of insulin will be administered to the upper third of the patient's nasal cavity. Thus, the present invention allows for a safe and efficacious treatment of a patient's PTSD where systemic administration is contraindicated or is otherwise undesirable.

Administration of intranasal insulin has been shown to improve memory in both normal adults and in patients with Alzheimer's disease. Recent studies have shown that insulin may enhance neuronal activity within the medio-temporal lobe and increase performance in humans under in-vivo conditions. The non-invasive intranasal method for bypassing the blood-brain barrier to target therapeutics (including insulin) to the brain to treat neurodegenerative disorders was first discovered by the inventor of the present disclosure, including the discovery, inter alia, applying intranasal insulin to the upper third of a patient's nasal cavity in order to target the CNS, e.g., brain, for treating and preventing Alzheimer's disease and certain other CNS disorders. Therapeutic agent(s) administered to the upper third of the patient's nasal cavity advantageously bypass the blood-brain barrier and rapidly reach the brain by traveling extracellularly along the olfactory and trigeminal neural pathways. This increases efficacy while reducing systemic exposure and unwanted side effects.

Intranasal insulin treatment improves memory in healthy adults with no change in the blood levels of insulin or glucose. For example, researchers in Germany have conducted several human clinical trials showing that intranasal insulin improves memory in normal adults. Intranasal insulin has been shown to improve memory in only twenty minutes after a single treatment in patients with Alzheimer's disease. Intranasal insulin has also been shown to improve memory, attention and functioning in Alzheimer's patients over a 21 day period, and improved memory and general cognition and reduced loss of brain FDG uptake in patients with Alzheimer's disease or amnestic mild cognitive impairment treated with intranasal insulin in a four month clinical trial with no change in the blood levels of insulin or glucose. It is noteworthy that the insulin in these studies was delivered generally intranasally, without specific targeting to the upper third of the patient's nasal cavity. Consequently, virtually all, i.e., in the range of 95% or greater, of the delivered insulin was administered to the lower two-thirds of the patient's nasal cavity and subsequently to the patient's system.

Intranasal insulin is likely an effective treatment and preventative for Alzheimer's disease because glucose uptake and utilization is significantly decreased in patients with Alzheimer's disease. Glucose is the only source of energy used by brain cells under normal conditions, and the brain cells of Alzheimer's patients are generally starved for energy. Alzheimer's disease has been shown to involve a deficiency of insulin and insulin signaling in the brain. Type II diabetes is a major risk factor for developing Alzheimer's disease.

When intranasal insulin, administered to the upper third of the patient's nasal cavity, reaches the brain, it stimulates the formation of insulin degrading enzyme (IDE), which is capable of degrading beta amyloid, one of the principle abnormal proteins known to accumulate in the brains of Alzheimer's patients. Further, the activity of glycogen-synthase kinase-3-beta, the enzyme that phosphorylates tau to create Alzheimer's neurofibrillary tangles, has been reported to be down-regulated in response to insulin. Insulin receptor signaling increases synaptic density, and loss of synapses is key to the neuropathology of Alzheimer's disease.

As discussed supra, stress has been similarly found to reduce the uptake and utilization of glucose by brain cells. It has further been found that glucocorticoids released in response to stress may damage neurons in the hippocampus. Multiple mechanisms are likely involved in this action; one of which is the inhibition of glucose uptake and/or glucose utilization in the hippocampus by glucocorticoids. Cortisol has been reported to reduce hippocampal glucose utilization in normal elderly adults based on examination of the brain glucose utilization (CMRglu) response to hydrocortisone (cortisol). It is likely that glucocorticoids also reduce the capacity of the hippocampus to survive in both primary and secondary hippocampal astrocytic cultures, and this could impair the ability of astrocytes to aid neurons by removing damaging glutamate from the synapse during times of neurologic crisis. Glucocorticoids released in response to major stress inhibit local cerebral glucose utilization throughout the brain and inhibit glucose transport in neurons, glia, and possibly endothelial cells in vitro. Most recently, glucocorticoids have been shown to induce PTSD-like memory impairments in mice.

In one study, general intranasal insulin (40 iu) treatment of 26 normal adult men minutes before they were exposed to the Trier Social Stress Test in placebo controlled, double-blind between-subject design, significantly diminished both the saliva and plasma cortisol response to the test. The amount of insulin was administered as follows: "Directly thereafter (50 min before TSST onset), either 0.4 ml (containing 40 I.U.) insulin (Actrapid1 100, Novo Nordisk) or a corresponding volume of placebo were administered intranasally to the participants." See Bohringer A., et al., "Intranasal insulin attenuates the hypothalamic-pituitary-adrenal axis response to psychosocial stress", Psychoneuroendocrinology, 2008 November; 33(10); 1394-400.

In the Bohringer study, the intranasal insulin was administered generally, i.e., to the lower two-thirds of the patient's nasal cavity. It is known that such general intranasal administration results in less than 5% of the administered dose reaching to the upper one third of the patient's nasal cavity allowing bypassing of the blood-brain barrier and extracellular transport along the olfactory and trigeminal neural pathways. The remaining more than 95% of the administered therapeutic agent is systemically absorbed and metabolized, with subsequent non-target organ involvement; a decidedly unwanted and potentially dangerous side effect. The end result is that a fraction of the therapeutic agent dose administered to the lower two thirds of the patient's nasal cavity actually reaches the blood-brain barrier barring entry to the patient's CNS. One of the consequences of this "general" intranasal administration for therapeutics is that precisely and accurately determining what concentration of the administered therapeutic actually is delivered to the target within the CNS is very difficult and is an estimate at best. This is suboptimal. The present invention corrects these, inter alia, deficiencies.

Thus, as a consequence, a large overdose must be administered to the lower two-thirds of the patient's nasal cavity in order to achieve what can be considered an "effective" dose or effective amount that is actually delivered to the target CNS, e.g., the brain. As stated previously, this overdosing produces unwanted, and potentially dangerous, side effects with inaccurate knowledge of the amount of the therapeutic actually delivered to the target within the CNS. In addition, the requirement that an overdose of a therapeutic agent in order to achieve close to an effective amount delivered to the target within the CNS is expensive.

Because intranasal insulin attenuates the hormonal response to stress in adult men, embodiments of the present disclosure provide for a way to treat and even protect against PTSD. Embodiments of the present disclosure use insulin nasal spray devices targeted to the upper third of the nasal cavity to treat individuals exposed to a traumatic stressful event shortly after it occurred or in other embodiments, to treat individuals, such as military personnel or first responders, who are at immediate high risk of traumatic stress, to help protect the brain against the damaging effects of such stress.

There are a variety of types of insulin available that may be used in accordance with the present disclosure, including insulins for which zinc is included for stabilization and others which do not include zinc. Because zinc may be detrimental to the olfactory system and may promote tau phosphorylation, insulins that do not contain zinc may be preferable in some cases. Formulations of insulin that either contain no preservatives (which could be prepared for unit dosing) or a safe preservative such as pyrophosphate are preferred. Acid sodium pyrophosphate is on the GRAS list for food additives and food preservatives. It is also sometimes referred to as disodium diphosphate and appears to bind metals such as iron and thus act as an antioxidant. At concentrations from about 1-5 µm, pyrophosphate protects the human brain muscarinic cholinergic receptor in vitro from inactivation by oxidants such as heme that are known to be elevated in the brains of patients with Alzheimer's disease. In some embodiments the insulin formulation may not include any phenol or cresol preservatives.

The neurologic agent—insulin—may be administered intranasally as a powder, spray, gel, ointment, infusion, injection, or drops, for example. The insulin may be administered in a dose comprising an effective amount of insulin as defined above. Such effective amounts may include for example, 0.1 IU, 1 IU, 5 IU, 10 IU, 20 IU, 40 IU, or more. The Bohringer study described above administered 40 IU. We may assume a specific activity of 27 units/mg for insulin generally. Thus, 40 units is the equivalent of approximately 1.5 mg. We further assume an average adult weighs about 75 kg, which results a dosing of approximately 0.02 mg/kg dose. Other trials and studies have administered 20 units, which, using the above assumption criteria, would be about 0.01 mg/kg dose. Still other trials and studies have used 10 units or about 0.005 mg/kg. Therefore, exemplary effective amounts for the present invention to be administered to the upper third of the patient's nasal cavity may be:

Efficacious dosage range: 0.0001-1.0 mg/kg.
A more preferred dosage range may be 0.002-1.0 mg/kg.
A further preferred dosage range may be 0.002-0.2 mg/kg.
A most preferred dosage range may be 0.002-0.1 mg/kg.

It will be understood, however, that any particular effective amount as defined above is contemplated and within the scope of the present disclosure. Doses of the effective amount of insulin may be administered immediately for example, from about one minute to about 120 minutes and any specific point there between prior to an anticipated stressful event, and/or from about one minute to about 120 minutes and any specific point there between after a stressful even has occurred. It will be understood that the disclosed times of about 1 to about 120 minutes pre- or post-event are not intended to be limiting and that doses may be administered at any useful time point before and/or after an event including less than a minute and greater than 120 minutes. The effective amount, including inter alia dosage volumes are discussed in further detail infra.

The intranasal composition may be dispensed as a powder or liquid nasal spray, nose drops, a gel or ointment, through a tube or catheter, by syringe, by packtail, by pledget, or by submucosal infusion. Any suitable nasal spray device targeting the upper third of the patient's nasal cavity may be used with embodiments of the present disclosure.

The composition may include the neurologic agent (insulin) as well as a vasoconstrictor that may generally enhance the efficiency of delivery of the intranasally delivered therapeutic compound comprising insulin.

Thus, constriction of blood vessels resulting from action of the vasoconstrictor in the nasal cavity facilitates transport of the therapeutic compound(s) comprising insulin into the brain along olfactory and trigeminal neural pathways, perivascular pathways, or lymphatic pathways. Thus, intranasal administration of a therapeutic compound(s) comprising insulin to the upper one third of a patient's nasal cavity in combination with the intranasal administration of an agent that constricts blood vessels (i.e. a vasoconstrictor) within or in the proximity of the mucosa of the nasal cavity enhances targeting of the intranasally delivered insulin to the CNS by reducing absorption into the blood, increasing CNS concentrations (as well as other targeted locations), or both.

In one embodiment, a pharmaceutical composition may be comprised of a combination of at least one therapeutic compound comprising insulin and at least one vasoconstrictor. In another embodiment, at least one vasoconstrictor may be applied intranasally or otherwise, i.e., intravenously, topically as a pretreatment or concurrently with administration of at least one therapeutic compound. A vasoconstrictor may be applied before intranasal administration of the effective dose of insulin, or in a pharmaceutical composition with the insulin dose. The use of a vasoconstrictor may improve the efficiency of delivery of the intranasally administered insulin to the patient's CNS, regardless of whether the intranasal delivery is to the lower two-thirds or upper one-third of the patient's nasal cavity.

Inclusion of vasoconstrictors in intranasal formulations or treatment method that include insulin for prevention and/or treatment of PTSD may include, but are not limited to providing the following advantages: reducing absorption into the blood, which is desirable for drugs with adverse side effects in the blood or in peripheral tissues; reducing systemic drug exposure, which is important for drugs that are rapidly eliminated in drug metabolizing organs or for drugs that are extensively bound to plasma proteins; targeting drugs to the olfactory epithelium for CNS delivery of drugs; reducing clearance of the drug into the blood from the nasal cavity, which increases the residence time and contact with the nasal epithelium; and targeting drugs to the olfactory epithelium, olfactory bulbs and/or anterior olfactory nucleus to have therapeutic potential for the treatment of PTSD; targeting the hippocampus for treatment of memory disorders associated with PTSD.

Exemplary vasoconstrictors in the various embodiments of the present invention may comprise, without limitation, PHE and/or THZ. Additional vasoconstrictors will be well known to the skilled artisan and may include, again without limitation, methoxamine, phenylephrine, ephedrine, norepinephrine, oxymatazoline, tetrahydrozoline, xylometazoline, clonidine, guanabenz, guanfacine, α-methyldopa, and/or arginine vasopressin.

An effective amount or dose as herein defined, of the therapeutic compound comprising insulin and/or vasoconstrictor to be administered pursuant to embodiments of the invention is the most preferred method of expression of dosage. Such effective amount is dependent upon many factors, including but not limited to, the type of disease or condition giving rise to an anticipated cerebral ischemia episode, the patient's general health, size, age, and the nature of the treatment, i.e. short-term or chronic treatment.

Generally, the treatment may be given in a single dose or multiple administrations, i.e., once, twice, three or more times daily over a period of time. In some cases, one or more doses daily may be given over an extended period of time, including, weeks or months. In other cases, the treatment may be given just prior to an anticipated event that may lead to development of PTSD and/or continued through the PTSD-inducing event and/or for a period of time following the PTSD-inducing event. These regimens thus encompass prevention of PTSD due to an anticipated impending or imminent event, protection of the CNS from PTSD during the PTSD-inducing event and further protection of the CNS from PTSD following the event, which may also be considered treatment of PTSD.

The method of the invention delivers the neurologic agent to the nasal cavity of a mammal; an exemplary and preferred mammal comprising a human being. In some embodiments, it is preferred that the insulin be delivered to the olfactory area in the upper third of the nasal cavity and particularly to the olfactory epithelium in order to promote transport of the agent along the peripheral olfactory axon bundles and into the perivascular channels to and throughout the CNS rather than into the capillaries within the respiratory epithelium. In some embodiments it may be preferable to transport insulin to the brain along the olfactory and trigeminal neural pathways instead of the circulatory system so that therapeutic agents that are unable to cross the blood-brain barrier from the bloodstream into the brain may be delivered to damaged neurons or neurons subject to damage in the brain.

The present invention in certain embodiments also enhances intranasal therapeutic compound delivery, e.g., insulin, to, inter alia, the olfactory epithelium, olfactory bulbs and lymphatics and enhances drug targeting to the olfactory epithelium, CNS, meninges and lymphatics by incorporating a vasoconstrictor into the nasal formulation and/or by applying a vasoconstrictor as a pretreatment to the intranasal application of the therapeutic compound. Thus, intranasal delivery of a therapeutic compound comprising insulin to the upper third of a patient's nasal cavity in combination with an agent that constricts blood vessels (i.e. a vasoconstrictor) within and around the nasal mucosa and nasal epithelium enhances intranasal drug targeting to the CNS, meninges and lymphatics by reducing absorption into the blood, increasing concentrations in selected regions of the CNS and in lymphatics, or both. Constriction of blood vessels resulting from action of the vasoconstrictor in the nasal cavity may facilitate efficiency of transport of the administered insulin into the brain along olfactory and trigeminal neural pathways, perivascular pathways, or lymphatic pathways.

This embodiment of the present invention delivers, administers and/or applies the therapeutic compound, comprising an effective amount of insulin, either alone or in combination with a vasoconstrictor to the nasal cavity of a mammal. It is preferred that the therapeutic compound comprising an effective amount of insulin, whether or not in combination with a vasoconstrictor be delivered to the olfactory neuroepithelium in order to promote rapid and efficient delivery of the therapeutic compound comprising insulin to the CNS along the olfactory neural pathway and to the respiratory and olfactory epithelium to promote rapid and efficient delivery of the therapeutic compound, vasoconstrictor and/or pharmaceutical composition to the CNS along the trigeminal neural pathway rather than into the capillaries within the nasal epithelium. Transport of an effective amount of the therapeutic compound comprising insulin, whether alone or in combination a vasoconstrictor and/or pharmaceutical composition to the brain by means of the olfactory and trigeminal neural pathways rather than the circulatory system is preferred so that harmful systemic side effects and potentially short half-life of the therapeutic agent comprising insulin in the blood are avoided. The preferred method allows direct delivery of various embodiments of the present invention to the CNS and to the meninges and lymphatics.

To deliver the therapeutic compound comprising insulin to the CNS, at least one effective amount of the therapeutic compound comprising insulin either alone or in combination with at least one vasoconstrictor wherein the vasoconstrictor(s) may be used as a pretreatment or simultaneously administered with the effective amount of insulin, may be administered to the nasal cavity, most preferably to the upper third of the patient's nasal cavity, though the vasoconstrictor may be administered to the lower two-thirds of the nasal cavity. In the present invention, the therapeutic compound comprises insulin. If applied to the upper third of the nasal cavity, the vasoconstrictor and/or therapeutic compound comprising insulin, comprising in certain embodiments a pharmaceutical composition of the present invention, is applied to the respiratory epithelium of the nasal cavity or to the olfactory epithelium located in the upper one-third of the nasal cavity. In all cases of application and/or administration, the composition may be administered intranasally as a powder or liquid spray, nose drops, a gel, lipid emulsion, lipid nanoparticles, lipid nanospheres or ointment, through a tube or catheter, by syringe, packtail, pledget or by submucosal infusion.

The optimal concentration of the active therapeutic agent, i.e., therapeutic compound comprising insulin, as well as the concentration of the vasoconstrictor when used in various embodiments, will necessarily depend upon, inter alia, the characteristics of the patient and the nature of the situation and/or condition, i.e., PTSD prevention and/or treatment for which the insulin is being used, though an effective amount is contemplated. In addition, the concentration will depend upon whether the agent is being employed in a preventive or treatment capacity. Further, the stage of a particular disease or disorder, e.g., prevention vs. treatment of PTSD, may dictate the optimal concentration of the therapeutic compound comprising insulin.

Thus certain embodiments of the present invention enhances targeting and efficiency of delivery of the effective amount of the therapeutic compound comprising insulin to the CNS by incorporating a vasoconstrictor into the nasal formulation, or by pre-treatment of the nasal cavity with the vasoconstrictor. Constriction of blood vessels resulting from action of the vasoconstrictor in the nasal cavity facilitates transport of the therapeutic compound(s) or agent(s) into the brain along olfactory and trigeminal neural pathways, perivascular pathways, or lymphatic pathways. Thus, administration to the upper third of a patient's nasal cavity of a therapeutic compound(s) comprising insulin in combination with an agent that constricts blood vessels (i.e. a vasoconstrictor) within or in the proximity of the mucosa of the nasal cavity enhances intranasal drug targeting to, inter alia, the CNS by reducing absorption into the blood, increasing CNS concentrations (as well as other targeted locations), or both.

Exemplary work performed according to one embodiment of the inventive method was performed as follows.

Exemplary Experiment and Data Set 1

Methods

We investigated whether incorporation of a vasoconstrictor (phenylephrine, PHE) in the nasal formulation enhances drug targeting of an intranasally applied neuropeptide (hypocretin-1, HC) to the brain in rodents. Several factors may effect CNS concentrations of HC following intranasal administration of HC in the presence of PHE, including the dose of vasoconstrictor, the time after intranasal delivery, and the pretreatment time interval. PHE is commonly used at a dose of 1% for nasal decongestion and topical nasal application of PHE results in a rapid onset of action and duration of action of approximately 4 hours. Ideally, it would be preferred to have a nasal formulation where the vasoconstrictor and CNS drug are administered together, without the need for pretreatment of the nasal cavity with vasoconstrictor. Clearly this would be more convenient than having to intranasally pretreat, wait a period of time (5 min or 15 min), and then intranasally administer the CNS drug with additional vasoconstrictor. However, waiting a short period of time may be a necessary step to allow the vasoconstrictor to activate adrenergic receptors located on blood vessels in the nasal cavity to result in constriction. Thus, in these experiments, three pretreatment time intervals were investigated: 0 min (or no pretreatment), 5 min, 15 min, to determine the time interval necessary to wait to allow the intranasally applied 1% PHE to take effect. Anesthetized rats were sacrificed at 30 minutes following intranasal delivery of HC and 1% PHE, since typically high brain concentrations are achieved within 25-30 minutes of intranasal administration.

Results & Discussion

Data Analysis

In order to determine if the pretreatment time interval had an effect on intranasal delivery to the CNS, one-way ANOVAs comparing tissue concentrations in the three groups (0 min, 5 min, 15 min) from the control animals were performed. One-way ANOVAs comparing tissue concentrations in the three groups from the PHE-treated animals were also performed. These statistical analyses demonstrated that the pretreatment time interval did not significantly affect intranasal delivery of HC to most CNS and peripheral tissues at the 30 minute sacrifice time point. Stated differently, the data demonstrate no therapeutic advantage from pretreatment with a vasoconstrictor. Thus, the therapeutic compound(s) and vasoconstrictor(s) may be combined in a pharmaceutical composition while retaining full therapeutic benefit of the present invention. Certain tissues such as the trigeminal nerve, superficial cervical lymph nodes, deep cervical lymph nodes, and dorsal and ventral meninges, were found to be statistically different from the other groups, however, these differences may be artifactual, since the majority of other tissues were unaffected by the pretreatment time interval. Pretreatment time interval also did not significantly affect delivery into the blood over the time course of the intranasal delivery experiments (FIG. 1). As a result, data obtained from control animals with different pretreatment time intervals were merged and data obtained from PHE-treated animals with different pretreatment time intervals were merged. Statistical comparisons were made between tissue concentrations in control animals (n=28) and PHE-treated animals (n=23).

Effect of 1% PHE on Site of Intranasal Administration (Blood, Nasal Epithelia, and Lymphatics)

Incorporation of 1% PHE into the nasal formulation significantly reduced absorption of HC into the blood (65% reduction) (FIG. 2), while significantly increasing concentrations in the olfactory epithelium (Table 1). It was also observed that 1% PHE significantly reduced concentrations in the respiratory epithelium compared to controls, as well as in the trigeminal nerve, which innervates the lateral walls and anterior portion of the nasal mucosa, in close relation to the respiratory epithelium (Table 1). Delivery to the nasal lymphatics was also significantly increased with 1% PHE, as observed by the increased concentration of HC in the superficial cervical lymph nodes and deep cervical lymph nodes (Table 1).

These results demonstrated significantly greater delivery of HC to the olfactory epithelium in the presence of 1% PHE. Thus, use of a vasoconstrictor is an alternative to expensive nasal delivery devices claiming to target therapeutics to the olfactory region of the nasal cavity. The increased deposition in the olfactory epithelium may be due to reduced clearance of the drug into the blood, thereby increasing the residence time of the formulation in the nasal cavity. Interestingly, these results also showed that delivery to the respiratory epithelium was significantly reduced compared to controls when vasoconstrictor was included in the nasal formulation. The respiratory mucosa, like the olfactory mucosa, is covered by a dense network of blood vessels. It was thought that the respiratory epithelium would also have a greater HC concentration in the PHE-treated animals compared to controls due to the reduced clearance of HC into the blood vessels in the respiratory mucosa. It is possible that in addition to reducing clearance of the drug into the blood and increasing the residence time in the nasal cavity, the vasoconstrictor opens up nasal passages due to its decongestant effects and allows more of the intranasally administered HC to reach the olfactory epithelium, and reduces the contact with the respiratory epithelium.

The blood concentration is significantly reduced in the presence of vasoconstrictor, so we would expect that the total nasal cavity concentration should be increased in PHE-treated animals compared to controls. When one looks at the total nasal cavity concentration, the concentration of HC is the same for the control and PHE-treated groups (24,162 vs. 24,787 nM); the difference is in the relative distribution of the drug within the nasal epithelia. Thus, it is more likely that the latter mechanism is primarily responsible for the increased deposition in the olfactory epithelium. It is possible that rather than staying in the nasal cavity, the therapeutic compound is channeled into the nasal lymphatics. In fact, concentrations in the superficial cervical lymph nodes and deep cervical lymph nodes, which are linked to the nasal cavity through lymphatic channels, were significantly increased in the presence of vasoconstrictor (Table 1). In summary, these results indicate that inclusion of a vasoconstrictor results in increased delivery to the olfactory epithelium and this is primarily due to the opening of the nasal passages, while increased delivery to the lymph nodes is primarily due to reduced clearance of the drug into the blood from the nasal cavity.

Effect of 1% PHE on Intranasal Delivery to the Brain and Lymphatics

Intranasal delivery of HC to the brain was affected by 1% PHE in the nasal formulation. HC concentrations in the olfactory bulbs doubled in the presence of 1% PHE, from 2.7 nM to 5.6 nM (p<0.05), likely due to the high concentration gradient present in the olfactory epithelium (Table 1). Delivery to other rostral brain regions, such as the anterior olfactory nucleus and frontal cortex, was unaffected by 1% PHE, though concentrations were slightly reduced (Table 1). It is possible that there was not enough time for the drug to diffuse to these regions and increased concentrations may have been achieved if animals were sacrificed at later times (i.e. at 60 or 120 minutes). Regions in the middle of the brain, including the hippocampus and hypothalamus, had significantly reduced concentrations of HC (Table 1). Moving to the caudal portions of the brain, such as the brainstem and cerebellum, it was found that concentrations were reduced (Table 1).

These data demonstrate that intranasal delivery to the rostral portion of the brain via the olfactory nerves is more dependent on the olfactory epithelium concentration than on the blood. The main driving force for absorption into the rostral brain is the high concentration gradient present in the olfactory epithelium, and as a result, a significant increase in olfactory bulb concentration was observed in PHE-treated animals. Results from these experiments also suggest an important role of the vasculature and/or the trigeminal nerve in intranasal delivery to middle and caudal brain regions, since significantly reducing blood concentrations also resulted in significantly reduced trigeminal nerve and brain concentrations. Trigeminal nerve and blood concentrations were linked: a 2.8-fold reduction in blood concentration resulted in a reduction in trigeminal nerve concentration of HC of the same magnitude Effect of 1% PHE on Delivery to Peripheral Tissue/Systemic Delivery With regard to exposure in peripheral tissues, intranasal delivery of HC with 1% PHE significantly reduced HC concentrations in the spleen and heart, while delivery to the liver and kidneys was unchanged in the presence of 1% PHE (Table 1). For therapeutic compounds, e.g., drugs that have adverse side effects due to widespread distribution in the body via the systemic circulation, vasoconstrictors in intranasal formulations may be a strategy to reduce systemic side effects due to the reduction in delivery to peripheral tissues and to the blood.

Effect of 1% PHE on Intranasal Drug Targeting to the CNS, Lymphatics, and Meninges Normalizing tissue concentrations to blood concentrations at 30 minutes provides an assessment of drug targeting to the tissue relative to the blood and allows for direct comparison between the control and PHE-treated groups (FIG. 3). Therapeutic compound targeting to nearly all CNS regions was significantly increased (p<0.05), with the greatest drug targeting to the rostral brain tissues such as the olfactory bulbs (6.8-fold), anterior olfactory nucleus (2.4-fold), and frontal cortex (2.3-fold) (FIG. 3). Therapeutic compound targeting to caudal brain tissues including the midbrain, medulla and cerebellum (1.7-fold) was increased compared to the control animals, (FIG. 3). Although delivery to the trigeminal nerve was reduced, as evidenced by lower concentrations with 1% PHE, drug targeting to the trigeminal nerve was not significantly different between control and PHE-treated groups (FIG. 3).

These results show that although absolute concentrations in the brain (excluding the olfactory bulbs) were reduced in the presence of a vasoconstrictor, blood concentrations were also significantly reduced, with the end result of increased intranasal therapeutic compound targeting to the brain. These results demonstrate that use of vasoconstrictors in intranasal formulations may be extremely valuable for targeting potent therapeutic compounds to the CNS, while reducing absorption into blood and widespread distribution to the rest of the body. For therapeutic compounds that are active at nanomolar concentrations, the reduction in brain concentrations should not significantly diminish the desired therapeutic response. For therapeutic compounds that have adverse effects in the blood or peripheral tissues, vasoconstrictors may be useful in preventing the drug from distributing to non-target sites where they can cause side effects. For therapeutic compounds that are extensively bound by plasma proteins or for biologics that are rapidly degraded by plasma proteases or drug metabolizing organs, vasoconstrictors can increase the availability of free and intact drug for absorption into the CNS.

The superficial and deep cervical lymph nodes were also significantly targeted with 1% PHE in the nasal formulation (5.7-fold increase for both, data not shown), which may be important for targeting immunotherapeutics to the lymphatic system. HC targeting after intranasal administration was also increased to the meninges (2.9-fold for ventral meninges, 1.7-fold for dorsal meninges) surrounding the brain, which could have therapeutic potential for targeting drugs to the meninges for the treatment of meningitis or encephalitis (data not shown). The fact that tissue-to-blood ratios were either increased or unchanged in CNS tissues, lymphatic tissues, and the meninges in the presence of 1% PHE suggests that incorporation of a vasoconstrictor into nasal formulations can improve drug targeting, and minimize targeting to the blood, which may be valuable for potent drugs that are accompanied by intolerable side effects in the blood and/or peripheral tissues.

Conclusion for Exemplary Experiment and Data Set 1

Incorporation of at least one vasoconstrictor in a nasal formulation including at least one therapeutic compound, i.e., a pharmaceutical composition, enhances intranasal therapeutic compounds targeting of therapeutics to, inter alia, the CNS, meninges and lymphatics by reducing absorption into the blood, increasing concentrations in, inter alia, the CNS, or both. Results from these experiments demonstrate that inclusion of a vasoconstrictor significantly enhances therapeutic compound delivery to the olfactory epithelium, olfactory bulbs and lymphatics and significantly enhances therapeutic compounds targeting to, inter alia, the CNS, meninges and lymphatics relative to blood following intranasal administration. In previous experiments comparing intravenous (IV) to intranasal (IN) delivery of HC in the absence of any additives, intranasal HC significantly targeted HC to the brain (Table 2, IN vs. IV). Inclusion of a vasoconstrictor in the intranasal formulation (IN PHE) further enhances brain targeting of HC compared to the intravenous delivery from the previous study (Table 2, IN PHE vs. IV). In addition, compared to intranasal delivery with no additives, intranasal administration of HC in combination with 1% PHE further enhances intranasal drug targeting to the brain, with increased targeting to the olfactory bulbs (7-fold increase), anterior olfactory nucleus (2-fold increase), frontal cortex (2-fold increase), hippocampus (2-fold increase), and hypothalamus (2-fold increase) (Table 2, IN PHE vs. IN). 1% PHE also enhances intranasal drug targeting to the superficial and deep cervical lymph nodes (5 to 6-fold) and to the meninges surrounding the brain (2-fold). Therefore, inclusion of a vasoconstrictor in an intranasal formulation is a novel strategy to further enhance intranasal drug targeting to the brain and lymphatics compared to other routes of administration. In addition, inclusion of a vasoconstrictor in the formulation is a novel strategy to selectively increase drug delivery to the olfactory epithelium, lymphatics and certain regions of the CNS including the olfactory bulbs without increasing delivery to other regions of the CNS including the hippocampus, pons, cerebellum or the trigeminal nerve.

Exemplary Experiment and Data Set 2

The vasoconstrictors selected for these experiments were tetrahydrozoline (THZ, MW 200), an imidazoline derivative, and phenylephrine (PHE, MW 204), an arylalkylamine derivative. Both vasoconstricting agents are α-adrenergic agonists with short duration of action (4-6 hours). The therapeutic compound selected was hypocretin-1 (HC, MW 3500), a peptide with therapeutic potential for treating narcolepsy. In addition to determining the effect of vasoconstrictors on the intranasal delivery of hypocretin-1 to the CNS, peripheral tissues and blood, vasoconstrictor effects on the drug targeting index (DTI) were also examined.

Methods

Studies of intranasal delivery of $^{125}$I-HC in the presence or absence of THZ or PHE to the CNS, peripheral tissues and blood were conducted in anesthetized adult male Sprague-Dawley rats. Thirty minutes following onset of intranasal delivery, rats were perfused with saline and fixed with 4% paraformaldehyde. Gamma counting was used to evaluate $^{125}$I-HC concentration and distribution in the CNS, peripheral tissues and blood. The DTI for each tissue was calculated by dividing the ratio of mean tissue concentration to blood area under the curve (AUC) of the vasoconstrictor group by the ratio of mean tissue concentration to blood AUC of the control group. DTI>1.0 indicated a drug targeting advantage with the vasoconstrictor.

Results

HC Plus 0.1% THZ (Refer to Table 3)

Addition of 0.1% THZ to the intranasal formulation of HC reduces elimination and clearance of HC from the olfactory epithelium into the bloodstream. 0.1% THZ significantly reduces the concentration in the blood at 5 min (1.1 nM vs. 0.4 nM, p=0.02) and significantly increases the concentration in the olfactory epithelium (1024 nM vs. 6744 nM, p=0.04) compared to controls. There is a significant increase in delivery to the olfactory bulbs (2.1 nM vs. 3.3 nM, p=0.03). In addition, there is a trend towards reducing delivery to the kidney (6.6 nM vs. 4.3 nM, p=0.08). The drug targeting index for the liver, kidney, spleen and thyroid are less than 1.0, indicating that there is reduced drug targeting to these peripheral organs in the presence of 0.1% THZ, thereby minimizing side effects and toxicity.

In addition, incorporation of 0.1% THZ in the intranasal formulation of HC resulted in fewer incidences of respiratory distress in animals during intranasal delivery.

HC Plus 0.1% THZ Following Pre-Treatment of Nasal Cavity with 0.1% THZ (Refer to Table 4)

Pre-treatment with and addition of 0.1% THZ to the intranasal formulation of HC reduces absorption of HC into the blood and reduces delivery of HC to peripheral organs. Delivery of HC to caudal brain tissues and the spinal cord is also reduced with pre-treatment with 0.1% THZ, while delivery to rostral brain tissues remains unchanged.

Absorption of HC into the blood is significantly decreased, particularly at 10 minutes (1.1 nM vs. 0.6 nM, p=0.03), 15 minutes (2.0 nM vs. 1.2 nM, p=0.01), and 20 minutes (3.1 nM vs. 2.1 nM, p=0.03).

Pre-treatment with 0.1% THZ significantly reduces delivery to the kidney (3.9 nM vs. 1.7 nM, p=0.01) and thyroid (276 nM vs. 68 nM, p=0.002). In addition, the drug targeting index for the muscle, kidney, spleen and thyroid are less than 1.0, indicating that there is reduced targeting to these peripheral organs by pre-treating the nasal cavity with 0.1% THZ. Significantly lower concentrations of HC are found in the trachea (49 nM vs. 2.0 nM, p=0.003) and esophagus (130 nM vs. 0.7 nM, p=0.06) and it was observed that there was significantly fewer signs of respiratory distress in rats treated with 0.1% THZ.

Pre-treatment of the nasal cavity with 0.1% THZ, followed by intranasal delivery of HC plus 0.1% THZ results in significantly reduced delivery to caudal brain regions, including the trigeminal nerve (5.5 nM vs. 2.0 nM, p=0.01), midbrain (0.7 nM vs. 0.5 nM, p=0.07), pons (0.8 nM vs. 0.5 nM, p=0.06) and cerebellum (0.6 nM vs. 0.4 nM, p=0.07). Additionally, significantly less HC is delivered to the upper cervical spinal cord (0.9 nM vs. 0.4 nM, p=0.002) and thoracic spinal cord (0.3 nM vs. 0.2 nM, p=0.06). Thus, 0.1% THZ reduces delivery to caudal brain regions, while having no effect on rostral brain regions such as the olfactory bulbs, anterior olfactory nucleus and frontal cortex. Inclusion of vasoconstrictors in the intranasal formulation of drugs provides a means to target delivery of therapeutic agents to specific brain regions.

HC Plus 1% PHE Following Pre-Treatment of Nasal Cavity with 1% PHE (Refer to Table 4)

Pre-treatment with and addition of 1% PHE to the intranasal formulation of HC reduces elimination and clearance from the olfactory epithelium into the bloodstream. Delivery of HC to caudal brain regions is also reduced with pre-treatment with 1% PHE, while delivery to rostral brain regions is unaffected.

Pre-treatment of the nasal cavity with 1% PHE significantly decreases absorption of therapeutic compound HC into the blood stream at all time points (5 min: 0.3 nM vs. 0.03 nM, p=0.004, 10 min: 1.1 nM vs. 0.2 nM, p<0.001, 15 min: 2.0 nM vs. 0.3 nM, p<0.001, 20 min: 3.2 nM vs. 0.9 nM, p<0.001, 30 min: 3.2 nM vs. 1.1 nM, p<0.001). The deposition of HC in the olfactory epithelium is significantly enhanced (3861 nM vs. 14847 nM, p<0.001) following pre-treatment with 1% PHE.

In addition, pre-treatment of the nasal cavity with 1% PHE, followed by intranasal delivery of HC plus 1% PHE significantly decreases delivery of HC to the trigeminal nerve (5.5 nM vs. 2.2 nM, p=0.005) and caudal brain tissues, including the hippocampus (0.6 nM vs. 0.4 nM, p=0.005), thalamus (0.6 nM vs. 0.4 nM, p=0.008), hypothalamus (1.4 nM vs. 0.7 nM, p=0.005), midbrain (0.7 nM vs. 0.5 nM, p=0.03), pons (0.8 nM vs. 0.5 nM, p=0.03), and cerebellum (0.6 nM vs. 0.4 nM, p=0.03).

Pre-treatment of the nasal cavity with 1% PHE results in an approximate 2.5 fold enhancement of therapeutic compound targeting to the central nervous system. 1% PHE enhances targeting to the brain and spinal cord, while significantly reducing absorption into the blood stream.

Pre-treatment with 1% PHE significantly reduces delivery of the therapeutic compound to peripheral organs including the spleen (0.9 nM vs. 0.6 nM, p=0.05) and thyroid (276 nM vs. 77 nM, p=0.003). In addition, the drug targeting index for the muscle is less than those for brain tissues, indicating that 1% PHE reduces targeting to the muscle, while enhancing targeting to the brain and spinal cord.

Pre-treatment with and use of 1% PHE significantly effects delivery of therapeutic compound HC to the lymphatic system. Pre-treatment with 1% PHE results in significant increases in delivery of HC to the superficial cervical lymph nodes (5.1 nM vs. 9.2 nM, p=0.05) and deep cervical lymph nodes (13 nM vs. 29 nM, p=0.04). 1% PHE also causes a significant decrease in delivery to the axillary lymph nodes (0.9 nM vs. 0.5 nM, p=0.006).

In addition, incorporation of 1% PHE in the intranasal formulation improved the consistency in delivery to the olfactory epithelium, but did not lead to any improvement in respiration during intranasal delivery.

Conclusion for Exemplary Experiment and Data Set 2

Use of 0.1% THZ in the formulation of HC and other therapeutic compounds decreases the amount of therapeutic compound entering the blood stream at early times, and thus reduces systemic exposure, exposure to peripheral tissues and unwanted systemic side effects. Use of 0.1% THZ increases targeting of the therapeutic compound to the olfactory epithelium and olfactory bulbs. In addition, there is reduced drug targeting to peripheral tissues (liver, kidney, spleen, thyroid).

Pre-treatment with and use of 0.1% THZ in the formulation of HC and other drugs significantly reduces absorption into the blood stream at most time points and decreases drug targeting to peripheral tissues. Pre-treatment with 0.1% THZ decreases delivery of HC to caudal portions of the brain, while leaving rostral portions unaffected. Incorporation of 0.1% THZ in the pharmaceutical composition also improves respiration in animals during intranasal delivery.

Pre-treatment with and use of 1% PHE in the formulation of HC and other therapeutic compounds significantly decreases the amount of drug entering the blood stream at all time points and thus reduces systemic exposure and unwanted systemic side effects. Pre-treatment with and use of 1% PHE in the formulation of HC and other therapeutic compounds enhances therapeutic compound targeting to the brain, spinal cord, olfactory epithelium and trigeminal nerve. Pre-treatment with and use of 1% PHE increases the consistency of delivery of therapeutic compounds to the brain, olfactory epithelium, olfactory bulbs, and trigeminal nerve.

Pre-treatment with and use of 1% PHE in the formulation of HC and other therapeutic compounds is more effective in reducing absorption into the blood stream and in enhancing therapeutic compound targeting to the brain and spinal cord compared to the use of 0.1% THZ.

Exemplary Experiment and Data Set 3

The effect of vasoconstrictors on intranasal drug targeting to the CNS of a smaller molecular weight therapeutic agent was also evaluated. We hypothesized that a therapeutic compound comprising a smaller peptide, which could more easily enter the blood, would be more affected by a vasoconstrictor than a therapeutic compound comprising a larger peptide. TP is a tripeptide with potent neuroprotective effects and is approximately one-tenth the size of HC.

Intranasal administration of $^{14}C$-TP in the presence of 1% PHE to anesthetized rats resulted in reduced absorption of therapeutic compound TP into the bloodstream at all time points over a 30 minute period (FIG. 4), which is consistent with our findings with HC discussed supra. In addition, 1% PHE reduced concentrations of TP in peripheral tissues including the lung, liver, heart, and kidney (FIG. 5).

In the presence of 1% PHE, intranasal targeting of TP, assessed by normalizing tissue concentrations to blood concentrations at 30 minutes, was increased to the olfactory epithelium, olfactory bulbs, rostral cortex and caudal cortex (Table 5). Drug targeting was also increased to the trigeminal nerve, meninges and lymphatics. With the exception of the increased drug targeting to the trigeminal nerve, these data with a considerably smaller peptide are consistent with the HC data. Therefore, the beneficial effect of a vasoconstrictor is not unique to HC and a vasoconstrictor can increase drug targeting with other therapeutic agents.

Exemplary Experiment and Data Set 4

We further evaluated the effect of vasoconstrictors on intranasal delivery of the therapeutic compound L-tyrosine-D-arginine, a stable dipeptide analog of the endogenous neuropeptide, kyotorphin (KTP, MW 337). KTP is a therapeutic compound demonstrating potent analgesic activity. The study investigated intranasal drug targeting of KTP to the CNS. First, to assess intranasal drug targeting of KTP to the CNS relative to intravenous administration, we compared the biodistribution of KTP following both routes of administration (n=6 to 7). Next, to assess if PHE enhances intranasal drug targeting of KTP to the CNS, we investigated the biodistribution of KTP following intranasal administration with 1% PHE (n=8). A higher concentration of PHE (5%) was also evaluated (n=6) to determine if the effect of the vasoconstrictor was dose dependent. Finally, CSF was sampled from a separate group of animals (n=4 to 6) after intravenous administration and intranasal administration of KTP in the presence and absence of 1% PHE.

Methods.

A mixture of unlabeled and $^{125}I$-labeled neuropeptide (KTP) was administered to anesthetized rats. CNS tissues, peripheral tissues, and blood were sampled following perfusion and fixation of animals approximately 30 minutes after the onset of drug delivery. Concentrations were determined based on radioactivity measured in tissues and blood by gamma counting. CNS tissue concentrations were normalized to blood concentrations at 30 minutes, providing an assessment of intranasal drug targeting to the CNS relative to the blood. Comparisons of concentrations and tissue-to-blood concentration ratios were made between different groups.

Animals.

Adult male Sprague-Dawley rats (200-300 g; Harlan, Indianapolis, Ind.) were housed under a 12-h light/dark cycle with food and water provided ad libitum. Animals were cared for in accordance with institutional guidelines and all experiments were approved by Regions Hospital, HealthPartners Research Foundation Animal Care and Use Committee.

Animal Surgeries.

Animals were anesthetized with sodium pentobarbital (Nembutal, 50 mg/kg intraperitoneal, Abbott Laboratories, North Chicago, Ill.). Body temperature was maintained at 37° C. by insertion of a rectal probe connected to a temperature controller and heating pad (Fine Science Tools, Inc., Foster City, Calif.). For intranasal and intravenous experiments, the descending aorta was cannulated for blood sampling and perfusion using a 20 G, 1¼ inch catheter (Jelco, Johnson and Johnson Medical Inc., Arlington, Tex.) connected to a 3-way stopcock (B. Braun Medical Inc., Bethlehem, Pa.). In addition, for intravenous experiments, the femoral vein was cannulated for drug administration using a 25 G, ¾ inch catheter (Becton Dickinson, Franklin Lakes, N.J.) connected to tubing and a 3-way stopcock (B. Braun Medical Inc., Bethlehem, Pa.).

Preparation of Formulations.

Intranasal and intravenous dose solutions contained a mixture of unlabeled and $^{125}$I-labeled neuropeptide (10 nmol, 50-55 µCi) dissolved in PBS (10 mM sodium phosphate, 154 mM sodium chloride, pH 7.4) to a final volume of 48 µL and 500 µL, respectively. For intranasal experiments with vasoconstrictor, 10% PHE (w/v) or 50% PHE (w/v) stock solutions were prepared and added to dose solutions containing neuropeptide to make a final concentration of 1% PHE or 5% PHE, respectively. Dose solution aliquots for each experiment were stored at −20° C. until the day of the experiment.

Drug Administration.

Intranasal administration was performed with animals lying on their backs and rolled gauze (1¼ cm diameter) placed under the neck to maintain rat head position, which prevented drainage of the dose solution into the trachea and esophagus. A pipette (P20) was used to intranasally administer 48 µL of dose solution over 14 minutes. Eight-6 µL nose drops were given to alternating nares every two minutes while occluding the opposite naris. This method of administration was non-invasive as the pipette tip was not inserted into the naris, but rather, the drop was placed at the opening allowing the animal to snort the drop into the nasal cavity. Intravenous administration through the femoral vein was performed with animals lying on their backs using an infusion pump (Harvard Apparatus, Inc., Holliston, Mass.) to administer 500 µL of a solution containing an equivalent dose over 14 minutes.

Tissue and Fluid Sampling.

Blood samples (0.1 mL) were obtained via the descending aorta cannula at 5, 10, 15, 20, and 30 minutes after the onset of drug delivery. After every other blood draw, 0.9% sodium chloride (0.35 mL) was replaced to maintain blood volume during the experiment.

Peripheral and CNS tissues were obtained at 30 minutes after the onset of drug delivery, following euthanasia of animals under anesthesia by perfusion and fixation through the descending aorta cannula with 60 mL of 0.9% sodium chloride and 360 mL of 4% paraformaldehyde in 0.1 M Sorenson's phosphate buffer using an infusion pump (15 mL/min; Harvard Apparatus, Inc., Holliston, Mass.). A gross dissection of major peripheral organs (muscle, liver, kidney, spleen, and heart) was performed, as well as dissection of the superficial and deep cervical lymph nodes and the axillary lymph nodes. The brain was removed and olfactory bulbs were dissected. Serial (2 mm) coronal sections of the brain were made using a rat brain matrix (Braintree Scientific, Braintree, Mass.). Microdissection of specific brain regions was performed on coronal sections using the Rat Brain Atlas as a reference. A posterior portion of the trigeminal nerve was dissected from the base of the cranial cavity from the anterior lacerated foramen to the point at which the nerve enters the pons. This tissue sample contained the trigeminal ganglion and portions of the ophthalmic (V1) and maxillary (V2) branches of the trigeminal nerve. Meninges from the spinal cord was removed and sampled prior to dissecting the spinal cord into cervical, thoracic, and lumbar sections. The left and right common carotid arteries were dissected from surrounding tissues with the aid of a dissection microscope. Each tissue sample was placed into a pre-weighed 5 mL tube, and the wet tissue weight was determined using a microbalance (Sartorius MC210S, Goettingen, Germany).

CSF was sampled via cisternal puncture at 30 minutes after the onset of drug delivery in a separate group of animals. Animals were placed on their ventral side over a rolled towel to position the head at a 45 degree angle. A 20 G needle attached to 30 cm long polyethylene tubing (PE90) was inserted into the cisterna magna. CSF was collected (~50 µL) into the tubing until flow stopped or until blood was observed. The tubing was immediately clamped if blood was observed to avoid contamination due to blood-derived radioactivity. Only CSF samples containing clear fluid were included in the analysis. Animals were perfused and fixed, and brain tissues were sampled as described above.

Sample and Data Analysis.

Radioactivity in each tissue sample was determined by gamma counting in a Packard Cobra II Auto Gamma counter (Packard Instrument Company, Meriden, Conn.). Concentrations were calculated, under the assumption of minimal degradation of the $^{125}$I-labeled neuropeptides, using the specific activity of the $^{125}$I-labeled neuropeptide determined from standards sampled from the dose solution, counts per minute measured in the tissue following subtraction of background radioactivity, and tissue weight in grams.

Dose-normalized concentrations in blood, CNS tissues, and peripheral tissues from intranasal and intravenous experiments at 30 minutes were expressed as mean±SE. Outliers were identified using the Grubbs statistical test for outliers and visually using box plots. The area under the blood concentration-time curve (AUC) from 0 to 30 minutes was calculated using the trapezoidal method without extrapolation to infinity. Since the concentrations observed in CNS after intranasal delivery could be due to absorption from the nasal vasculature and diffusion or receptor-mediated transport across the BBB, CNS tissue concentrations were normalized to blood concentrations at 30 minutes to assess direct transport from the nasal cavity. If the tissue-to-blood concentration ratios following intranasal delivery with PHE were observed to be greater than those after intravenous or intranasal administration without vasoconstrictor, then this would suggest that the vasoconstrictor enhances delivery along pathways other than vasculature. Intranasal drug targeting to the CNS could be enhanced with the vasoconstrictor if CNS tissue concentrations increased, if blood concentrations decreased or if both effects were observed. Unpaired two-sample t-tests were performed on concentrations and tissue-to-blood concentration ratios at 30 minutes to compare each group to intranasal control animals. Statistical analyses were performed using GraphPad Prism software (version 3.03, GraphPad Software Inc., San Diego, Calif.) and differences were significant if p<0.05.

Kyotorphin Biodistribution Following Intranasal and Intravenous Delivery. (See Table 6)

As illustrated by the data shown in Table 6 and accompanying figures, intranasal drug targeting of KTP to the CNS was confirmed by comparing intranasal and intravenous drug delivery. Intranasal compared to intravenous administration of KTP resulted in significantly lower concentrations in the blood at all time points measured (FIG. 6). Intranasal administration of KTP over 14 minutes resulted in a gradual increase in blood concentration, with a peak concentration of 11.7 nM at 30 minutes, while intravenous infusion resulted in a peak concentration of 83 nM at 10 minutes which steadily declined to 55 nM at 30 minutes. The resulting KTP blood AUC was significantly less following intranasal administration (145.30 nmol*min/L vs. 1708.83 nmol*min/L).

Intranasal administration resulted in KTP brain and spinal cord concentrations that were significantly lower than those after intravenous delivery (~3-fold); however the intravenous route was accompanied by 5-fold greater blood concentration. KTP brain concentrations after intranasal administration ranged from 1.8 nM to 4.3 nM, with the highest concentration in the olfactory bulbs. Intravenous brain concentrations ranged from 5.0 nM in the pons to 7.5 nM in the caudate/putamen. In the spinal cord, intranasal KTP resulted in a decreasing concentration gradient from the rostral to caudal direction, while intravenous delivery resulted in the highest concentration in the lumbar segment of the spinal cord. Distribution into the CSF and dorsal meninges were significantly greater with intravenous compared to intranasal administration.

In the nasal cavity, the respiratory and olfactory epithelia contained very high levels of KTP following intranasal compared to intravenous administration. Superficial cervical lymph node concentrations were significantly greater with intravenous delivery, while deep cervical lymph node concentrations of KTP were significantly greater with intranasal delivery. No statistically significant differences were noted in trigeminal nerve concentrations (p=0.41), although KTP levels were slightly elevated in the intranasal group. Additionally, no statistically significant differences were observed in carotid artery concentrations; however concentrations were higher with intranasal delivery (p=0.13).

In peripheral tissues, intranasal delivery of KTP resulted in significantly lower concentrations compared to intravenous administration. The kidneys contained the highest peripheral tissue concentration of KTP, regardless of route of administration.

Kyotorphin Biodistribution with and without PHE.

Inclusion of PHE in intranasal formulations reduced absorption of KTP into the blood compared to intranasal KTP controls (FIG. 6). 1% PHE significantly reduced the KTP blood concentration at 30 minutes to 5.1 nM (56% reduction) and the blood AUC to 71.48 nmol*min/L (51% reduction). With 5% PHE, KTP blood concentration at 30 minutes was further reduced to 4.0 nM (66% reduction) and the KTP blood AUC was further reduced to 45.65 nmol*min/L (69% reduction) compared to intranasal KTP controls (FIG. 6).

PHE dose dependently increased concentrations of KTP in the olfactory bulbs to levels higher than those achieved with intravenous delivery, while reducing concentrations in most remaining brain regions (Table 6). As illustrated further by the data in Table 6, 1% PHE did not significantly affect concentrations of KTP in the anterior olfactory nucleus, but the presence of the vasoconstrictor significantly reduced concentrations by half to all remaining brain regions, as well as to the spinal cord. Similar trends were observed with 5% PHE, except fewer CNS tissues were significantly different from intranasal KTP controls. 1% PHE reduced KTP concentrations in the CSF from 0.5 nM to 0.3 nM, but these differences were only marginally significant (p=0.09). The effect of 5% PHE on CSF distribution of KTP was not evaluated. CSF concentrations of KTP were relatively low in comparison to concentrations in the brain, regardless of the route of drug administration. No significant effects on KTP concentrations in the meninges were noted with PHE.

Referring again to Table 6, in the nasal cavity, PHE dose dependently increased deposition in the olfactory epithelium. KTP olfactory epithelium concentrations were found to be predictive of olfactory bulb concentrations, with a positive correlation coefficient of 0.99 (data not shown). 1% PHE significantly increased KTP concentrations in the respiratory epithelium, while 5% PHE had no significant effect. PHE significantly increased KTP concentrations in superficial cervical lymph nodes from 6.5 nM to 21 nM with 1% PHE and to 13 nM with 5% PHE. KTP concentrations in the deep cervical lymph nodes were slightly elevated with PHE; however differences were not significant. Cervical lymph node concentrations were among the highest observed outside of the CNS following intranasal administration. No statistically significant differences were noted in trigeminal nerve concentrations with PHE; however these values were slightly reduced in the presence of vasoconstrictor. Additionally, no significant differences were observed in carotid artery concentrations, though 1% PHE reduced concentrations, while 5% PHE had little effect.

PHE significantly reduced exposure of KTP to all peripheral tissues sampled (except the heart with 5% PHE). Similar reductions in peripheral tissue concentrations were observed with 1% PHE and 5% PHE, with the greatest reduction in the kidney and liver.

Kyotorphin Drug Targeting to the CNS, Lymphatics, and Meninges.

Intranasal compared to intravenous administration of KTP resulted in significantly greater brain tissue-to-blood concentration ratios, and 5% PHE, but not 1% PHE, significantly enhanced intranasal drug targeting of KTP to the brain and to the trigeminal nerve (See FIG. 7). The intranasal route of administration targeted KTP to the CNS compared to intravenous delivery, with the greatest tissue-to-blood concentration ratios in the trigeminal nerve (TN) and the olfactory bulbs (OB), while intravenous administration resulted in relatively uniform ratios throughout the CNS. 1% PHE significantly increased olfactory bulb ratios (5.3-fold increase) compared to intranasal KTP controls. No other significant differences in drug targeting were observed with 1% PHE (FIG. 10). With 5% PHE, intranasal drug targeting of KTP was increased to many more CNS tissues (FIG. 10). Compared to controls, 5% PHE significantly increased ratios in the olfactory bulbs (16.1-fold), anterior olfactory nucleus (AON, 3.2-fold), frontal cortex (FC, 2.3-fold), hippocampus (HC, 1.5-fold), hypothalamus (3.8-fold), and cerebellum (CB, 2.1-fold). In the spinal cord, drug targeting to the cervical spinal cord was increased with 5% PHE, but only marginally (p=0.07). Intranasal drug targeting was also significantly increased to the trigeminal nerve with 5% PHE (2.2-fold) (FIG. 7). Inclusion of 1% PHE or 5% PHE in nasal formulations also significantly enhanced targeting to the superficial nodes (5.1-fold and 4.6-fold, respectively) and to the cervical lymph nodes (3.0-fold and 4.8-fold, respectively) compared to intranasal KTP controls (data not shown). 1% PHE or 5% PHE also significantly enhanced targeting of KTP to the meninges, with slightly greater targeting to the ventral portion (3.6-fold and 3.4-fold, respectively) compared to the dorsal portion (2.3-fold and 3.2-fold, respectively).

Conclusion for Exemplary Experiment and Data Set 4

Our results indicate that over a 30 minute period, inclusion of a vasoconstrictor in the nasal formulation, or applied as a pretreatment prior to administering the therapeutic compound, drastically reduced blood concentrations and enhanced intranasal delivery to the CNS along olfactory neural pathways, while reducing transport along trigeminal pathways. PHE dose dependently increased concentrations of HC and KTP in the olfactory epithelium and olfactory bulbs, consistent with entry along olfactory nerves through the cribriform plate, suggesting that deposition in the olfactory region is critical for efficient delivery of intranasally applied drugs to rostral brain regions. Intranasal drug targeting, assessed by tissue-to-blood concentration ratios, was enhanced with PHE in certain CNS tissues, mainly due to the reduction in blood concentrations observed in the presence of the vasoconstrictor. Targeting to the olfactory bulbs was significantly greater with the 1% PHE formulation for HC and KTP. Enhanced drug targeting with 1% PHE was noted for HC throughout the brain, while no other significant differences in targeting of KTP was observed. These findings indicate that, at least for two therapeutic compounds comprising neuropeptides with different molecular weights, inclusion of a vasoconstrictor in nasal formulations can enhance drug targeting to rostral brain areas. Inclusion of PHE in the nasal formulation also enhanced drug targeting of HC and KTP to the lymphatic system and to the meningeal membranes surrounding the brain.

The data indicate that inclusion of a short-acting vasoconstrictor in a nasal formulation enhanced intranasal drug delivery and targeting to the olfactory bulbs, while significantly reducing absorption into the blood over a 30 minute time period, irrespective of the size of the therapeutic peptide, i.e., therapeutic compound administered. These findings provide additional evidence for olfactory-mediated pathways into rostral portions of the brain following intranasal administration. In addition, this work implicates mechanisms involving the trigeminal nerve and/or vasculature in intranasal delivery of therapeutics to the CNS. This novel strategy for enhancing intranasal delivery to the CNS using vasoconstrictors may be most suitable for potent CNS therapeutics that have adverse effects in the blood or peripheral tissues, that are rapidly degraded by enzymes in the blood or the gastrointestinal tract, or that are extensively bound by tissue or plasma proteins. Vasoconstrictor nasal formulations containing therapeutic compounds can be used to target brain tumors or to treat pain disorders, avoiding undesirable side effects that often accompany traditional routes of drug administration. Inclusion of vasoconstrictors in nasal formulations can result in enhanced therapeutic compound targeting to multiple brain areas, the lymphatic system, and the meninges, which may hold relevance for the treatment of various neurological disorders, autoimmune disorders, or meningitis.

OVERALL CONCLUSIONS

Intranasal administration, either targeting the upper one-third or lower two-thirds of the nasal cavity and/or without regard to intranasal target location(s), of therapeutics results in greater therapeutic compound or agent targeting to the CNS compared to intravenous delivery, and incorporation of a vasoconstrictor in the nasal formulation significantly enhances therapeutic compound targeting to the CNS, meninges and lymphatics, while significantly reducing absorption into the blood. This may be due to reduced clearance into the blood from the nasal cavity or due to decongestion of the nasal passages, allowing for increased residence time and contact with the olfactory mucosa. The potential application of vasoconstrictors in intranasal formulations are immense for highly potent drugs that have adverse effects in the blood or in peripheral tissues, that are rapidly degraded in the blood or in drug metabolizing organs, or that are extensively bound to plasma proteins. Vasoconstrictors could be used in nasal formulations of chemotherapeutics targeting brain tumors or with pain medications that target the brain and spinal cord, but that with traditional routes of administration, also result in undesirable side effects in patients. These data also show that intranasal delivery of immunotherapeutics in combination with a vasoconstrictor may be a successful drug targeting strategy to the immune system, as certain diseases involve the breakdown of the immune system and new therapeutics are emerging that activate the adaptive immune response to reject CNS tumors. We hypothesized that inclusion of a vasoconstrictor in nasal formulations, i.e., pharmaceutical compositions, would reduce absorption into the blood, increase the residence time of the therapeutic compound, e.g., drug, in the nasal epithelium, and facilitate intranasal delivery into the brain along pathways involving the olfactory nerves, trigeminal nerves, CSF or nasal lymphatic channels.

Several CNS-related disorders, diseases and/or conditions may be prevented, or the effects minimized, using different embodiments of the present invention. For example, and without limitation, patients at risk for developing PTSD, including those facing imminent high-stress situations, e.g., first responders, may be aided by the technique.

In another embodiment, at least one vasoconstrictor may be applied intranasally or otherwise, i.e., intravenously, topically as a pretreatment or concurrently with administration of an effective amount of at least one therapeutic compound comprising insulin. Further, an effective amount of at least one therapeutic compound comprising insulin may be combined with at least one vasoconstrictor to form a pharmaceutical compound that may be administered following pretreatment with intranasally (or intravenously, topically, etc.,) administered vasoconstrictor and/or concurrently with such vasoconstrictor.

Exemplary vasoconstrictors in the various embodiments of the present invention may comprise, without limitation, PHE and/or THZ. Additional vasoconstrictors will be well known to the skilled artisan and may include, again without limitation, methoxamine, phenylephrine, ephedrine, norepinephrine, oxymetazoline, tetrahydrozoline, xylometazoline, clonidine, guanabenz, guanfacine, α-methyldopa and/or arginine vasopressin.

An effective amount, as herein defined, of the therapeutic compound and/or vasoconstrictor to be administered pursuant to embodiments of the invention is the most preferred method of expression of dosage. Such effective amount is dependent upon many factors, including but not limited to, the type of disease or condition, the patient's general health, size, age, and the nature of treatment, i.e., short-term of chronic treatment. For illustrative purposes only, exemplary treatment regimens relating generally to the therapeutic compounds comprising insulin disclosed herein, including dosage ranges, volumes and frequency are provided below, referencing the disclosure regarding effective amounts for the present invention described supra:

Efficacious dosage range: 0.0001-1.0 mg/kg.
A more preferred dosage range may be 0.002-1.0 mg/kg.
A further preferred dosage range may be 0.002-0.2 mg/kg.
A most preferred dosage range may be 0.002-0.1 mg/kg.
The dosage volume (applicable to nasal sprays or drops) range may be 0.015 mls-1.0 mls.

The preferred dosage volume (applicable to nasal sprays or drops) range may be 0.03-0.6 mls.

The efficacious vasoconstrictor dosage may be 0.0001-0.3 mg/kg.

Generally, the treatment may be given in a single dose or multiple administrations, i.e., once, twice, three or more times daily over a period of time. For patients chronically afflicted with PTSD, the treatment may consist of at least one dose per day over an extended period of time. Alternatively, for those patients anticipating a high-stress condition or situation such as a first responder, the treatment may be a one-time dose to precondition the CNS in anticipation of potential cerebral ischemia.

The brain concentrations that are likely to be achieved with the dosage ranges provided above are, for a single dose: 0.1 nM-50 µM. Over the course of a multi-dose treatment plan, the maximum brain concentration may be as high as 500 µM.

Inclusion of vasoconstrictors in intranasal formulations containing CNS therapeutic compounds comprising an effective amount of insulin for prevention and/or treatment of PTSD:

(1) Reduces absorption of insulin into the blood, which is desirable to minimize adverse side effects in the blood or in peripheral tissues as well as expense;
(2) Reduces systemic insulin exposure to minimize rapidly eliminating insulin in drug metabolizing organs;
(3) In the embodiment comprising a vasoconstrictor: targets insulin to the olfactory epithelium, reducing the need for expensive drug delivery devices that claim to target drugs to olfactory epithelium for CNS delivery of drugs;
(4) Reduces clearance of the insulin into the blood from the nasal cavity, which increases the residence time and contact with the nasal epithelium;
(5) Targets insulin to the olfactory epithelium, olfactory bulbs and/or anterior olfactory nucleus for direct deliver to the CNS in order to have maximum therapeutic potential for the prevention and/or treatment of PTSD;
(6) Targets insulin delivery to the frontal cortex to reach brain targets involved in PTSD;
(7) Targets insulin delivery to the hippocampus for the treatment of learning and memory disorders associated with PTSD and other neurologic disorders;
(8) Targets insulin delivery to the hypothalamus for the treatment of PTSD;
(9) Targets drugs to the cerebellum and brainstem for treating PTSD.

TABLE 1

CONCENTRATIONS OF HC FOLLOWING INTRANASAL ADMINISTRATION IN THE PRESENCE AND ABSENCE OF 1% PHE

| Concentration (nM) | Intranasal HC Control Mean ± SE | Intranasal HC + 1% PHE Mean ± SE |
|---|---|---|
| Brain | | |
| Olfactory Bulbs | 2.68 ± 0.33 | 5.60 ± 0.49 * |
| Anterior Olfactory Nucleus | 1.11 ± 0.14 | 0.89 ± 0.07 |
| Frontal Cortex | 0.93 ± 0.09 | 0.69 ± 0.08 |
| Caudate/Putamen | 0.58 ± 0.08 | 0.40 ± 0.07 |
| Septal Nucleus | 0.88 ± 0.32 | 0.54 ± 0.12 |
| Parietal Cortex | 0.67 ± 0.07 | 0.39 ± 0.04 * |
| Hippocampus | 0.61 ± 0.06 | 0.32 ± 0.02 * |
| Thalamus | 0.60 ± 0.05 | 0.30 ± 0.02 * |
| Hypothalamus | 1.04 ± 0.11 | 0.68 ± 0.06 * |
| Midbrain | 0.65 ± 0.06 | 0.38 ± 0.03 * |
| Pons | 0.93 ± 0.14 | 0.44 ± 0.04 * |
| Medulla | 1.26 ± 0.22 | 0.76 ± 0.11 * |
| Cerebellum | 0.67 ± 0.07 | 0.38 ± 0.04 * |
| Spinal Cord | | |
| Cervical | 0.80 ± 0.12 | 0.96 ± 0.27 |
| Thoracic | 0.35 ± 0.03 | 0.19 ± 0.03 * |
| Lumbar | 0.35 ± 0.02 | 0.17 ± 0.01 * |
| Cerebrospinal Fluid | | |
| Cerebrospinal Fluid | 0.17 ± 0.02 | 0.28 ± 0.04 * |
| Meninges | | |
| Dorsal Meninges | 2.71 ± 0.33 | 1.51 ± 0.19 * |
| Ventral Meninges | 7.47 ± 1.19 | 7.54 ± 1.29 |
| Spinal Meninges | 2.66 ± 0.59 | 4.58 ± 1.47 |
| Nasal Epithelia | | |
| Respiratory Epithelium | 19921 ± 1758 | 11457 ± 1348 * |
| Olfactory Epithelium | 4241 ± 628 | 13330 ± 905 * |
| Lymphatic System | | |
| Superficial Cervical Nodes | 3.56 ± 0.25 | 6.50 ± 0.69 * |
| Deep Cervical Nodes | 18.29 ± 3.94 | 35.58 ± 3.54 * |
| Trigeminal Nerve | | |
| Trigeminal Nerve | 4.93 ± 0.70 | 1.71 ± 0.15 * |
| Blood Vessels | | |
| Carotid Arteries | 82.70 ± 13.13 | 256 ± 135 |
| Peripheral Tissues | | |
| Blood | 3.38 ± 0.16 | 1.19 ± 0.08 * |
| Muscle | 0.53 ± 0.05 | 0.40 ± 0.10 |
| Liver | 0.76 ± 0.05 | 0.69 ± 0.04 |
| Kidney | 3.00 ± 0.30 | 2.75 ± 0.47 |
| Spleen | 0.89 ± 0.06 | 0.50 ± 0.04 * |
| Heart | 0.37 ± 0.06 | 0.18 ± 0.02 * |

$p < 0.05$, unpaired t-test comparing intranasal HC + 1% PHE with intranasal HC control

TABLE 2

ENHANCED DRUG TARGETING WITH VASOCONSTRICTOR IN THE INTRANASAL FORMULATION

| DRUG TARGETING | IN vs. IV Fold Difference | IN PHE vs. IV Fold Difference | IN PHE vs. IN Fold Difference |
|---|---|---|---|
| Olfactory Epithelium | 3176 | 31852 | 10 |
| Trigeminal Nerve | 12 | 12 | 1.0 |
| Olfactory Bulbs | 11 | 72 | 6.8 |
| Anterior Olfactory Nucleus | 6.7 | 16 | 2.3 |
| Frontal Cortex | 5.1 | 12 | 2.3 |
| Hippocampus | 3.9 | 6.0 | 1.5 |
| Hypothalamus | 5.9 | 11 | 1.8 |
| Pons | 5.6 | 9.0 | 1.6 |
| Cerebellum | 5.0 | 7.0 | 1.4 |
| Upper Cervical Spinal Cord | 17.4 | 16 | 0.9 |
| Lower Cervical Spinal Cord | 4.5 | 14 | 3.0 |
| Thoracic Spinal Cord | 2.7 | 4.7 | 1.7 |
| Lumbar Spinal Cord | 1.8 | 2.5 | 1.4 |
| Dorsal Meninges | 8.3 | 12 | 1.5 |
| Ventral Meninges | 16 | 37 | 2.3 |
| Superficial Lymph Nodes | 5.6 | 32 | 5.7 |
| Deep Cervical Lymph Nodes | 32 | 164 | 5.1 |
| Axillary Lymph Nodes | 0.9 | 1.3 | 1.3 |

Drug targeting = $(Brain/blood)_{intranasal}/(Brain/blood)_{intravenous}$

TABLE 3

CONCENTRATIONS OF HC FOLLOWING INTRANASAL ADMINISTRATION IN THE ABSENCE
AND PRESENCE OF 0.1% THZ WITH NO PRETREATMENT OF THE NASAL CAVITY

| CONCENTRATION (nM) | Control n = 4, 43 μL, 40 μCi, 10 nmol | | 0.1% THZ-treated n = 4, 44 μL 43 μCi, 11 nmol | | * p < 0.05 |
|---|---|---|---|---|---|
| | MEAN | SE | MEAN | SE | |
| Blood at 30 minutes | 5.61 | 0.86 | 5.82 | 0.52 | |
| Olfactory Epithelium | 1023.94 | 462.33 | 6744.60 | 2132.99 | * |
| Trigeminal Nerve | 5.38 | 1.12 | 3.43 | 0.63 | |
| Olfactory Bulbs | 2.11 | 0.24 | 4.82 | 1.55 | |
| Anterior Olfactory Nucleus | 1.13 | 0.08 | 1.50 | 0.42 | |
| Frontal Cortex | 1.31 | 0.12 | 1.46 | 0.39 | |
| Hippocampus | 0.71 | 0.03 | 0.87 | 0.31 | |
| Hypothalamus | 1.89 | 0.14 | 1.97 | 0.58 | |
| Pons | 0.90 | 0.05 | 0.83 | 0.25 | |
| Cerebellum | 0.75 | 0.05 | 0.79 | 0.24 | |
| Upper Cervical Spinal Cord | 1.40 | 0.15 | 1.22 | 0.62 | |
| Lower Cervical Spinal Cord | 0.78 | 0.36 | 0.60 | 0.15 | |
| Thoracic Spinal Cord | 0.48 | 0.15 | 0.33 | 0.02 | |
| Lumbar Spinal Cord | 0.49 | 0.12 | 0.37 | 0.03 | |
| Dorsal Meninges | 3.35 | 0.48 | 3.88 | 1.00 | |
| Ventral Meninges | 6.46 | 1.95 | 6.68 | 1.39 | |
| Superficial Lymph Nodes | 14.86 | 2.82 | 21.97 | 4.77 | |
| Deep Cervical Lymph Nodes | 24.70 | 6.83 | 24.38 | 6.36 | |
| Axillary Lymph Nodes | 1.36 | 0.13 | 1.30 | 0.36 | |
| Muscle | 0.65 | 0.16 | 0.74 | 0.22 | |
| Liver | 1.89 | 0.30 | 1.85 | 0.27 | |
| Kidney | 6.56 | 0.87 | 5.55 | 1.28 | |
| Spleen | 3.75 | 2.10 | 1.27 | 0.18 | |

* $p < 0.05$, unpaired t-test between control and 0.1% THZ-treated

TABLE 4

CONCENTRATIONS OF HC FOLLOWING INTRANASAL ADMINISTRATION IN THE ABSENCE
AND PRESENCE OF VASOCONSTRICTORS WITH PRETREATMENT OF THE NASAL CAVITY

| CONCENTRATION (nM) | Control n = 7, 48 μL 40 μCi, 10 nmol | | 0.1% THZ-treated n = 8, 48 μL, 40 μCi, 10 nmol | | 1% PHE-treated n = 8, 48 μL, 40 μCi, 10 nmol | |
|---|---|---|---|---|---|---|
| | MEAN | SE | MEAN | SE | MEAN | SE |
| Blood at 30 minutes | 3.16 | 0.32 | 3.23 | 0.81 | 1.09[#] | 0.07 |
| Olfactory Epithelium | 3860.77 | 1376.05 | 3834.99* | 1866.37 | 14846.60[#] | 958.80 |
| Trigeminal Nerve | 5.48 | 0.75 | 2.02* | 0.64 | 2.23[#] | 0.60 |
| Olfactory Bulbs | 3.52 | 0.90 | 3.55 | 1.54 | 6.54 | 1.36 |
| Anterior Olfactory Nucleus | 1.33 | 0.23 | 0.79 | 0.16 | 0.90 | 0.13 |
| Frontal Cortex | 1.26 | 0.15 | 0.84 | 0.21 | 0.94 | 0.15 |
| Hippocampus | 0.63 | 0.07 | 0.45 | 0.06 | 0.38[#] | 0.04 |
| Hypothalamus | 1.35 | 0.16 | 0.81 | 0.20 | 0.73[#] | 0.10 |
| Pons | 0.81 | 0.10 | 0.49 | 0.09 | 0.51[#] | 0.08 |
| Cerebellum | 0.63 | 0.06 | 0.44 | 0.06 | 0.43[#] | 0.06 |
| Upper Cervical Spinal Cord | 1.36 | 0.45 | 0.40 | 0.06 | 1.36 | 0.50 |
| Lower Cervical Spinal Cord | 0.54 | 0.23 | 0.24 | 0.03 | 0.89 | 0.42 |
| Thoracic Spinal Cord | 0.32 | 0.05 | 0.21 | 0.03 | 0.21 | 0.05 |
| Lumbar Spinal Cord | 0.33 | 0.02 | 0.27 | 0.04 | 0.18[#] | 0.02 |
| Dorsal Meninges | 2.89 | 0.55 | 1.97 | 0.75 | 1.71 | 0.43 |
| Ventral Meninges | 6.71 | 1.32 | 4.75 | 1.93 | 6.52 | 2.56 |
| Superficial Lymph Nodes | 5.06 | 1.16 | 9.03 | 2.53 | 9.15[#] | 1.43 |
| Deep Cervical Lymph Nodes | 12.89 | 2.07 | 12.68 | 5.50 | 29.01[#] | 6.31 |
| Axillary Lymph Nodes | 0.94 | 0.13 | 0.65 | 0.08 | 0.50[#] | 0.05 |
| Muscle | 1.21 | 0.78 | 0.33 | 0.07 | 0.46 | 0.17 |
| Liver | 0.88 | 0.11 | 0.72 | 0.11 | 0.82 | 0.06 |
| Kidney | 3.93 | 0.68 | 1.73* | 0.26 | 3.47 | 0.96 |
| Spleen | 0.88 | 0.13 | 0.65 | 0.07 | 0.57[#] | 0.07 |

*$p < 0.05$, unpaired t-test between control and 0.1% THZ-treated;
[#]$p < 0.05$, unpaired t-test between control and 1% PHE-treated

TABLE 5

TISSUE-TO-BLOOD RATIOS OF TP FOLLOWING
INTRANASAL ADMINISTRATION IN THE ABSENCE
AND PRESENCE OF 1% PHE

| TISSUE-TO-BLOOD RATIO | Control (n = 2) MEAN | SE | PHE-treated (n = 2) MEAN | SE |
|---|---|---|---|---|
| Olfactory Epithelium | 1741.73 | 257.59 | 10622.99 | 6537.86 |
| Trigeminal Nerve | 2.82 | 0.24 | 11.30 | 2.88 |
| Olfactory Bulbs | 9.04 | 4.78 | 45.77 | 4.18 |
| Rostral Cortex | 0.90 | 0.26 | 2.05 | 0.18 |
| Caudal Cortex | 0.82 | 0.09 | 1.03 | 0.09 |
| Hippocampus | 0.93 | 0.17 | 0.93 | 0.19 |
| Midbrain | 0.94 | 0.17 | 1.23 | 0.06 |
| Pons | 0.96 | 0.14 | 1.31 | 0.29 |
| Cerebellum | 1.06 | 0.15 | 1.22 | 0.20 |
| Upper Cervical Spinal Cord | 1.38 | 0.71 | 1.08 | 0.19 |
| Lower Cervical Spinal Cord | 0.68 | 0.05 | 0.56 | 0.01 |
| Thoracic Spinal Cord | 0.55 | 0.07 | 0.52 | 0.09 |
| Lumbar Spinal Cord | 0.56 | 0.12 | 0.51 | 0.07 |
| Ventral Meninges | 7.84 | 1.85 | 63.96 | 19.36 |
| Superficial Lymph Nodes | 2.98 | 1.15 | 27.33 | 9.16 |
| Deep Cervical Lymph Nodes | 34.35 | 10.08 | 99.63 | 15.07 |

TABLE 6

CONCENTRATIONS OF KTP FOLLOWING INTRAVENOUS
ADMINISTRATION AND INTRANASAL ADMINISTRATION
OF KTP IN THE PRESENCE AND ABSENCE OF PHE

| Concentration (nM) | Intravenous KTP Mean ± SE | Intranasal KTP Control Mean ± SE | Intranasal KTP + 1% PHE Mean ± SE | Intranasal KTP + 5% PHE Mean ± SE |
|---|---|---|---|---|
| Brain | | | | |
| Olfactory Bulbs | 6.88 ± 0.69 + | 4.33 ± 0.59 | 12.85 ± 3.28 * | 24.48 ± 4.64 # |
| Anterior Olfactory Nucleus | 6.18 ± 0.75 + | 2.42 ± 0.26 | 2.04 ± 0.41 | 2.70 ± 0.42 |
| Frontal Cortex | 6.60 ± 1.93 + | 2.24 ± 0.23 | 1.34 ± 0.20 * | 1.81 ± 0.23 |
| Caudate/Putamen | 7.54 ± 0.53 + | 2.13 ± 0.22 | 0.88 ± 0.13 * | 1.08 ± 0.29 # |
| Septal Nucleus | 6.64 ± 0.23 + | 2.09 ± 0.16 | 1.24 ± 0.12 * | 1.27 ± 0.21 # |
| Parietal Cortex | 7.30 ± 0.82 + | 2.53 ± 0.12 | 1.13 ± 0.16 * | 1.28 ± 0.22 # |
| Hippocampus | 6.20 ± 0.67 + | 1.90 ± 0.20 | 0.89 ± 0.12 * | 0.98 ± 0.20 # |
| Thalamus | 6.22 ± 0.75 + | 1.83 ± 0.19 | 0.86 ± 0.11 * | 1.49 ± 0.49 |
| Hypothalamus | 7.03 ± 0.77 + | 2.63 ± 0.25 | 1.66 ± 0.26 * | 3.64 ± 1.31 |
| Midbrain | 5.64 ± 0.62 + | 1.92 ± 0.18 | 0.96 ± 0.14 * | 1.49 ± 0.41 |
| Pons | 4.97 ± 0.17 + | 1.90 ± 0.09 | 0.86 ± 0.13 * | 1.97 ± 0.68 |
| Medulla | 5.33 ± 0.47 + | 1.87 ± 0.20 | 0.89 ± 0.14 * | 1.87 ± 0.57 |
| Cerebellum | 5.98 ± 0.66 + | 2.10 ± 0.09 | 0.87 ± 0.12 * | 1.37 ± 0.29 # |
| Spinal Cord | | | | |
| Cervical | 4.99 ± 0.72 + | 1.62 ± 0.40 | 0.64 ± 0.17 * | 1.37 ± 0.40 |
| Thoracic | 4.34 ± 0.49 + | 1.27 ± 0.24 | 0.52 ± 0.10 * | 0.50 ± 0.07 # |
| Lumbar | 5.46 ± 0.71 + | 1.20 ± 0.13 | 0.46 ± 0.06 * | 0.45 ± 0.03 # |
| Cerebrospinal Fluid | | | | |
| Cerebrospinal Fluid | 2.23 ± 0.17 + | 0.49 ± 0.09 | 0.27 ± 0.06 | — |
| Meninges | | | | |
| Dorsal Meninges | 6.26 ± 1.11 + | 4.34 ± 0.71 | 3.96 ± 0.84 | 6.43 ± 1.65 |
| Ventral Meninges | 10.32 ± 1.23 | 16.66 ± 3.20 | 20.45 ± 2.91 | 20.22 ± 4.50 |
| Spinal Meninges | 10.12 ± 3.00 | 5.59 ± 1.94 | 3.48 ± 0.95 | 2.88 ± 0.77 |
| Nasal Epithelia | | | | |
| Respiratory Epithelium | 19.94 ± 7.12 + | 21419 ± 2564 | 36853 ± 5734 * | 15908 ± 1702 |
| Olfactory Epithelium | 30.67 ± 1.61 + | 1988 ± 676 | 5754 ± 1165 * | 12492 ± 381 # |
| Lymphatic System | | | | |
| Superficial Cervical Nodes | 10.50 ± 1.23 + | 6.45 ± 0.62 | 20.89 ± 3.39 * | 13.24 ± 1.32 # |
| Deep Cervical Nodes | 10.24 ± 1.15 + | 61.58 ± 18.42 | 71.48 ± 12.27 | 93.59 ± 12.01 |
| Trigeminal Nerve | | | | |
| Trigeminal Nerve | 9.44 ± 0.49 | 12.54 ± 3.33 | 7.68 ± 1.47 | 8.63 ± 1.61 |
| Blood Vessels | | | | |
| Carotid Artery | 18.74 ± 3.37 | 155.55 ± 77.26 | 69.20 ± 43.96 | 165.44 ± 56.57 |
| Peripheral Tissues | | | | |
| Blood | 54.88 ± 2.15 + | 11.68 ± 1.33 | 5.12 ± 0.47 * | 3.98 ± 0.30 # |
| Muscle | 13.62 ± 6.77 + | 2.20 ± 0.22 | 1.42 ± 0.23 * | 0.68 ± 0.04 # |
| Liver | 25.34 ± 4.66 + | 6.38 ± 1.12 | 1.70 ± 0.23 * | 1.58 ± 0.20 # |
| Kidney | 143.76 ± 50.94 + | 49.54 ± 9.46 | 7.19 ± 1.90 * | 7.39 ± 0.98 # |

TABLE 6-continued

CONCENTRATIONS OF KTP FOLLOWING INTRAVENOUS
ADMINISTRATION AND INTRANASAL ADMINISTRATION
OF KTP IN THE PRESENCE AND ABSENCE OF PHE

| Concentration (nM) | Intravenous KTP Mean ± SE | Intranasal KTP Control Mean ± SE | Intranasal KTP + 1% PHE Mean ± SE | Intranasal KTP + 5% PHE Mean ± SE |
|---|---|---|---|---|
| Spleen | 12.51 ± 3.18 + | 3.58 ± 0.72 | 1.26 ± 0.14 * | 1.49 ± 0.16 # |
| Heart | 3.72 ± 0.47 + | 1.46 ± 0.20 | 0.81 ± 0.08 * | 1.15 ± 0.25 |

+, *, # $p < 0.05$, unpaired t-test comparing each group with intranasal KTP control The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method for treating a patient for Post-Traumatic Stress Disorder (PTSD) resulting from witnessing an event, the witnessed event consisting of an occupational situation involving violence, serious injury, and/or death, comprising:
identifying the patient witnessing the event;
providing at least one effective amount of a therapeutic compound comprising an insulin;
during the patient's witnessing of the event, administering the at least one effective amount of the therapeutic compound comprising an insulin to the upper one-third of the nasal cavity of the patient, thereby enabling the administered at least one effective amount of the therapeutic compound comprising an insulin to bypass the patient's blood-brain barrier; and
thereby enabling delivery of the at least one effective amount of the therapeutic compound comprising an insulin to the patient's central nervous system (CNS) to treat the patient for PTSD during the patient's witnessing of the event.

2. A method for treating a patient for PTSD resulting from the witnessing of an event consisting of an occupational situation involving violence, serious injury, and/or death comprising:
identifying the event and the patient who will witness the event;
providing at least one effective amount of a therapeutic compound comprising an insulin;
before the patient witnesses the event, administering the at least one effective amount of the therapeutic compound comprising an insulin to the upper one-third of the nasal cavity of the patient, thereby enabling the administered at least one effective amount of the therapeutic compound comprising an insulin to bypass the patient's blood-brain barrier; and
thereby enabling delivery of the at least one effective amount of the therapeutic compound comprising an insulin to the patient's central nervous system (CNS) to treat the patient for PTSD before the patient witnesses the event.

3. The method of claim 2, wherein the therapeutic compound comprising insulin does not contain zinc.

4. The method of claim 3, wherein the insulin is glulisine.

5. The method of claim 2, further comprising administering a vasoconstrictor to the patient.

6. The method of claim 5, wherein the at least one vasoconstrictor comprises tetrahydrozoline.

7. The method of claim 5, wherein the at least one vasoconstrictor comprises phenylephrine.

8. The method of claim 5, wherein the vasoconstrictor is administered intranasally to the patient.

9. The method of claim 5, wherein an effective amount of the vasoconstrictor dosage is within the range of 0.0001-0.3 mg/kg.

10. The method of claim 2, wherein the therapeutic compound comprising an insulin further comprises pyrophosphate for preservation and is prepared for unit dosing to administer the at least one effective amount.

11. The method of claim 2, wherein the therapeutic compound comprising an insulin does not contain a cresol or a phenol preservative and is prepared for unit dosing to administer the at least one effective amount.

12. The method of claim 2, wherein an effective amount of the insulin is within the range: 0.0001-1.0 mg/kg.

13. The method of claim 12, wherein a dosage range for the therapeutic compound comprising an insulin is within the range of 0.002-0.1 mg/kg.

14. The method of claim 12, wherein a dosage range for the therapeutic compound comprising an insulin is within the range of 0.03-0.6 mls.

15. The method of claim 2, wherein an effective amount of the insulin is within the range 0.002-1.0 mg/kg.

16. The method of claim 2, wherein an effective amount of the insulin is within the range 0.002-0.2 mg/kg.

17. The method of claim 2, wherein administration of the at least one effective amount of the therapeutic compound comprising insulin results in a brain concentration of insulin in the range of 0.1 nM-50 µM.

18. The method of claim 2, further comprising administering at least one additional effective amount of the therapeutic compound comprising an insulin to the upper one-third of the nasal cavity of the patient during the witnessing of the event.

19. The method of claim 2, further comprising administering at least one additional effective amount of the therapeutic compound comprising an insulin to the upper one-third of the nasal cavity of the patient for a period of time following the witnessing of the event.

* * * * *